United States Patent [19]

Mangelsdorf et al.

[11] Patent Number: 5,723,329
[45] Date of Patent: Mar. 3, 1998

[54] DNA ENCODING RETINOID RECEPTOR X (RXR) ALPHA AND GAMMA; CORRESPONDING VECTORS AND HOST CELLS

[75] Inventors: David J. Mangelsdorf, San Diego; Ronald M. Evans, La Jolla, both of Calif.

[73] Assignee: The Salk Institute for Biological Studies, La Jolla, Calif.

[21] Appl. No.: 336,408

[22] Filed: Nov. 8, 1994

Related U.S. Application Data

[63] Continuation of Ser. No. 933,453, Aug. 21, 1992, abandoned, which is a continuation of Ser. No. 478,071, filed as PCT/US91/00399, Jan. 22, 1991, abandoned.

[51] Int. Cl.$^6$ .............................. C12N 15/12; C12N 5/10
[52] U.S. Cl. ..................... 435/240.2; 435/326.1; 435/69.1; 435/69.7; 536/23.5
[58] Field of Search ........................... 536/23.5, 24.1; 435/69.1, 320.1, 240.2, 69.7

[56] References Cited

U.S. PATENT DOCUMENTS

| | | |
|---|---|---|
| 4,981,784 | 1/1991 | Evans et al. ............................ 435/6 |
| 5,171,671 | 12/1992 | Evans et al. ........................ 435/69.1 |
| 5,274,077 | 12/1993 | Evans et al. ........................ 530/350 |
| 5,403,925 | 4/1995 | Ozato ............................... 536/23.5 |

OTHER PUBLICATIONS

Mangelsdorf et al, Nature, v. 345, May 17, 1990, p. 224.
Hazel et al, Proc. Natl. Acad. Sci. USA, v. 85, Nov. 1988, p. 8444.
Giguere et al., "Identification of a receptor for the morphogen retinoic acid", Nature vol. 330:624–629 (1987).
Giguere et al., "Identification of a new class of steroid hormone receptors", Nature vol. 331:91–94 (1988).
Hazel et al., "A gene inducible by serum growth factors encodes a member steroid and thyroid hormone receptor superfamily", Proc. natl. Acad. Sci. USA vol. 85:8444–8448 (1988).
Giguere et al., "Spatial and temporal expression of the retinoic acid receptor in the regenerating amphibian limb", Nature vol. 337:566–569 (1989).
Hamada et al., "H–2RIIBP, a member of the nuclear hormone receptor superfamily that binds to both the regulatory element of major histocompatibility class I genes and the estrogen response element", Proc. Natl. Acad. Sci. USA vol. 86:8289–8293 (1989).

*Primary Examiner*—David L. Fitzgerald
*Attorney, Agent, or Firm*—Pretty, Schroeder, Brueggemann & Clark; Stephen E. Reiter

[57] ABSTRACT

The present invention relates to novel receptor polypeptides, which, upon interaction with certain ligands, or activation by certain compounds, modulate transcription of certain genes by binding to cognate response elements associated with promoters of such genes. The novel receptors of the invention modulate transcription in the presence of retinoid compounds. The receptors of the present invention differ significantly from known retinoic acid receptors, in protein primary sequence and in responsiveness to exposure to various retinoids. The invention provides DNAs encoding the novel receptors, expression vectors for expression of the receptors, cells transformed with such expression vectors, cells co-transformed with such expression vectors and with reporter vectors to monitor modulation of transcription by the receptors, and methods of using such co-transformed cells in screening for compounds which are capable, directly or indirectly, of activating the receptors. The invention also provides nucleic acid probes for identifying DNAs which encode additional retinoid receptors of the same class as the novel receptors disclosed herein.

17 Claims, 9 Drawing Sheets

1

DNA ENCODING RETINOID RECEPTOR X (RXR) ALPHA AND GAMMA; CORRESPONDING VECTORS AND HOST CELLS

RELATED APPLICATIONS

This application is a continuation of application U.S. Ser. No. 07/933,453, filed Aug. 21, 1992, now abandoned; which is a continuing application of U.S. Ser. No. 07/478,071, filed Feb. 9, 1990, now abandoned, and PCT Ser. No. US91/00399, filed Jan. 22, 1991, the entire contents of which are hereby incorporated by reference herein.

TECHNICAL FIELD

The present invention concerns novel, steroid hormone-like receptor proteins and methods of making and using same.

More particularly, the invention relates to steroid hormone-like receptor proteins with transcription-modulating effects. Such proteins are responsive to the presence of retinoic acid and other vitamin A metabolites.

BACKGROUND OF THE INVENTION

The retinoids comprise a group of compounds including retinoic acid, retinol (vitamin A), and a series of natural and synthetic derivatives that together exert profound effects on development and differentiation in a wide variety of systems. Although early studies focused on the effects of retinoids on growth and differentiation of epithelial cells, their actions have been shown to be widespread. Many recent studies have examined the effects of these molecules on a variety of cultured neoplastic cell types, including the human promyelocytic leukemia cell line, HL60, where retinoic acid appears to be a potent inducer of granulocyte differentiation. In F9 embryonal carcinoma cells, retinoic acid will induce the differentiation of parietal endoderm, characteristic of a late mouse blastocyst. Retinoic acid also appears to play an important role in defining spatio-temporal axes in the developing avian limb and the regenerating amphibian limb.

Retinoic acid has been shown to induce the transcription of several cDNAs whose gene products have been isolated by differential screening. This observation supports the hypothesis that retinoic acid exerts its action via modulation of gene expression, in a manner analogous to the way in which steroid and thyroid hormones influence their target genes.

The ability to identify compounds which affect transcription of genes which are responsive to retinoic acid or other metabolites of vitamin A, would be of significant value, e.g., for therapeutic applications. Further, systems useful for monitoring solutions, body fluids and the like for the presence of retinoic acid, vitamin A or metabolites of the latter would be of value in various analytical biochemical applications and, potentially, medical diagnosis.

Through molecular cloning studies it has been possible to demonstrate that receptors for steroid, retinoid and thyroid hormones are all structurally related. These receptors comprise a superfamily of regulatory proteins that are capable of modulating specific gene expression in response to hormone stimulation by binding directly to cis-acting elements (Evans, Science 240, 889 (1988); Green and Chambon, Trends genet. 4, 309 (1988)). Structural comparisons and functional studies with mutant receptors have established that these molecules are composed of discrete functional domains, most notably, a DNA-binding domain that is composed typically of 66–68 amino acids (including two zinc fingers), and an associated carboxy terminal stretch of approximately 250 amino acids which comprises the ligand-binding domain (reviewed in Evans, supra).

Low-stringency hybridization has permitted the isolation and subsequent delineation of a growing list of gene products which possess the structural features of hormone receptors.

Recently, a retinoic acid dependent transcription factor, referred to as RAR-alpha (retinoic acid receptor-alpha), has been identified. Subsequently, two additional RAR-related genes have been isolated; thus there are now at least three different RAR subtypes (alpha, beta and gamma) known to exist in mice and humans. These retinoic acid receptors (RARs) share homology with the superfamily of steroid hormone and thyroid hormone receptors and have been shown to regulate specific gene expression by a similar ligand-dependent mechanism (Umesono et al., Nature 336, 262 (1988)). These RAR subtypes are expressed in distinct patterns throughout development and in the mature organism.

Other information helpful in the understanding and practice of the present invention can be found in commonly assigned, co-pending U.S. patent application Ser. Nos. 108,471, filed Oct. 20, 1987, now issued as U.S. Pat. No. 5,071,773; 276,536, filed Nov. 30, 1988, now issued as U.S. Pat. No. 4,981,784; 325,240, filed Mar. 17, 1989, now abandoned; 370,407, filed Jun. 22, 1989, now U.S. Pat. No. 5,260,432; and 438,757, filed Nov. 16, 1989, now issued as U.S. Pat. No. 5,091,518, all of which are hereby incorporated herein by reference in their entirety.

SUMMARY OF THE INVENTION

We have discovered novel receptors which are activated to modulate transcription of certain genes in animal cells, when the cells are exposed to retinoids, such as retinoic acid and retinal. The novel receptors differ significantly from known retinoic acid receptors, both in terms of the primary protein sequence and responsiveness to various retinoids.

The novel receptors have several isoforms located at genetically distinct loci. They are capable of transactivating through cis elements similar to retinoic acid receptors, but show a different rank potency and dose dependency to retinoids. Northern analyses of the novel receptors of the present invention indicate that each isoform has a unique pattern of expression in adult tissue and is temporally and spatially expressed in the embryo. Binding experiments demonstrate that the novel receptor proteins have a low affinity for [$^3$H]retinoic acid. These results, taken together with results from transactivation studies, suggest the ligand (s) for the novel receptors is a metabolite(s) or structural analog(s) of retinoic acid. The invention provides DNAs encoding novel receptors, expression vectors for expression of the receptors, cells transformed with such expression vectors, cells co-transformed with such expression vectors and reporter vectors to monitor modulation of transcription by the receptors, and methods of using such co-transformed cells in screening for compounds which are capable, directly or indirectly, of activating the receptors.

The invention also provides single-stranded nucleic acid probes for identifying DNAs encoding additional retinoid receptors.

The invention also provides a method for making the receptors of the invention by expressing DNAs which encode the receptors in suitable host organisms.

Animal cells in which receptors of the invention are present can be employed to assay fluids for the presence of retinoids. Animal cells of the invention can also be employed to screen compounds of potential therapeutic value for their ability to bind and/or promote transactivation (i.e., trans-acting transcriptional activation) by the receptors of the invention.

As will be described in greater detail below, the receptors of the invention modulate transcription of genes. This occurs upon binding of receptor to hormone response elements, which are positioned operatively, with respect to promoters for such genes, for such modulation to occur. Among hormone response elements contemplated for use in the practice of the present invention are $TRE_p$, the beta-retinoic acid response element, and the estrogen response element, as well as closely related elements which are disclosed, for example, in application Ser. No. 438,757, filed Nov. 16, 1989, now issued as U.S. Pat. No. 5,091,518, and application Ser. No. 325,240, filed Mar. 17, 1989, now abandoned.

DETAILED DESCRIPTION OF THE INVENTION

Figure 1:
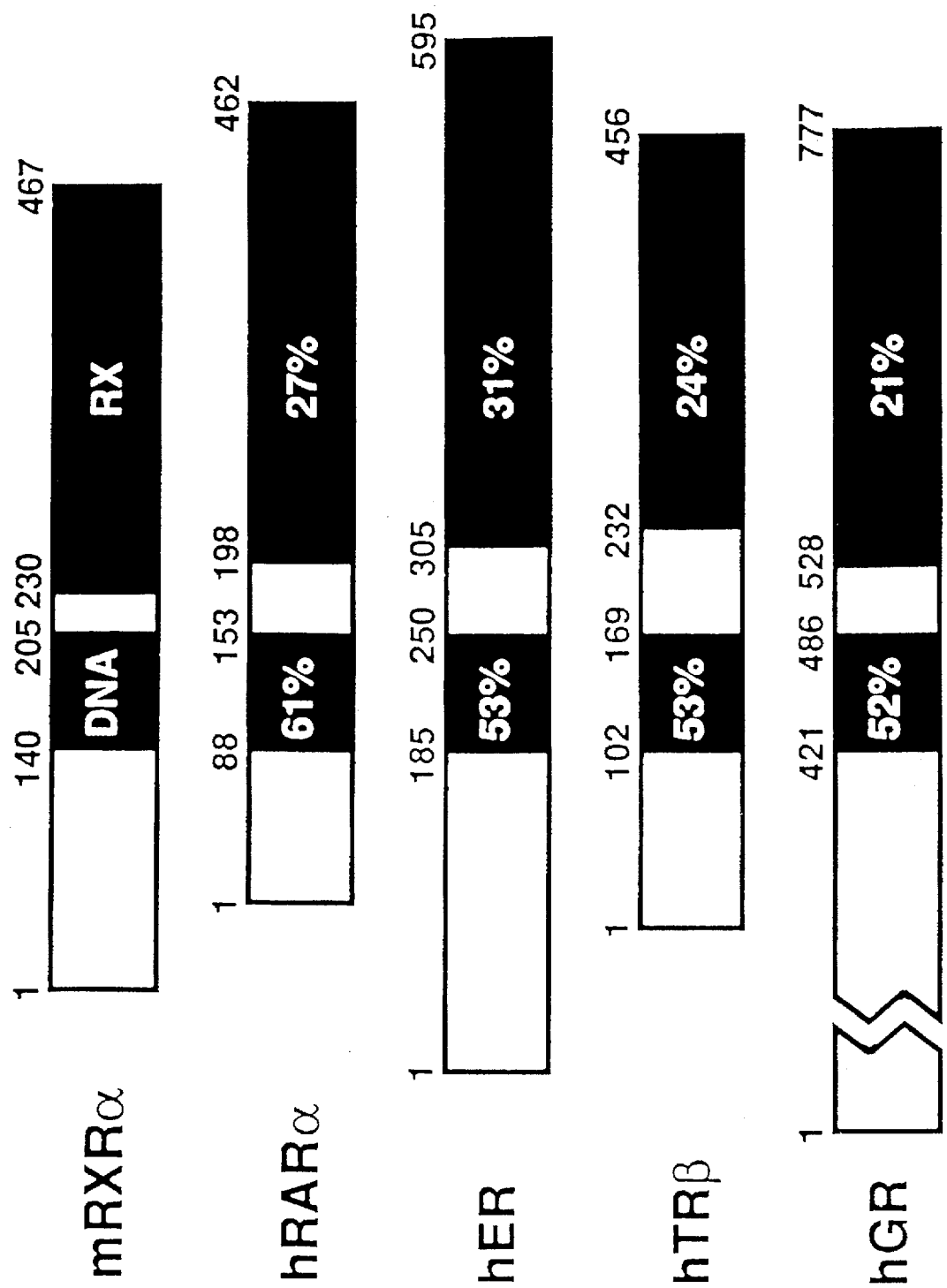
FIG. 1 shows the extent of amino acid identity (i.e., "homology") between the DNA binding domain ("DNA") and ligand binding domain ("RX") of mouse RXR-alpha (mRXRα), relative to the corresponding domains of human retinoic acid receptor-alpha (hRARα), human estrogen receptor (hER), human thyroid hormone receptor-beta (hTRβ) and human glucocorticoid receptor (hGR).

The invention concerns novel polypeptides, which are characterized by:

(1) being responsive to the presence of retinoid(s) to regulate transcription of associated gene(s);

(2) having a DNA binding domain of about 66 amino acids with 9 Cys residues, wherein said DNA binding domain has:
   (a) less than about 65% amino acid identity with the DNA binding domain of hRAR-alpha,
   (b) less than about 55% amino acid identity with the DNA binding domain of hTR-beta, and
   (c) less than about 55% amino acid identity with the DNA binding domain of hGR; and (3) not including the sequence set forth in Sequence ID No 7.

The novel polypeptide receptors of the present invention can be further characterized in a variety of ways, e.g., by increasing the rate of transcription of a target gene in a construct comprising a promoter operatively linked to a hormone response element for transcriptional activation by said receptors, relative to the rate of transcription in the absence of said receptor and/or in the absence of retinoic acid and retinal. Transcription of said target gene is measured in an animal cell in culture, the medium of which comprises retinoic acid or retinal at a concentration greater than about $5 \times 10^{-7}$M.

Alternatively, the polypeptide receptors of the present invention can be further characterized as being encoded by a continuous nucleotide sequence which encodes substantially the same amino acid sequence as that of amino acids 1–462 shown in Sequence ID No. 2 [hRXRα], amino acids 1–467 shown in Sequence ID No. 4 [mRXRα], or amino acids 1–463 shown in Sequence ID No. 6 [mRXRγ].

As yet another alternative, the polypeptide receptors of the present invention can be characterized as being encoded by a continuous nucleotide sequence which encodes substantially the same amino acid sequence as that of amino acids 135–200 shown in Sequence ID No. 2 [DNA binding domain of hRXRα], amino acids 140–205 shown in Sequence ID No. 4 [DNA binding domain of mRXRα], or amino acids 139–204 shown in Sequence ID No. 6 [DNA binding domain of mRXRγ].

As still another alternative, the polypeptide receptor of the present invention can be characterized as being encoded by a continuous nucleotide sequence which is substantially the same as nucleotides 76–1464 shown in Sequence ID No. 1 [hRXRα], nucleotides 181–1581 shown in Sequence ID No. 3 [mRXRα], or nucleotides 123–1514 shown in Sequence ID No. 5 [mRXRγ].

Chimeric receptors of the steroid/thyroid hormone receptor superfamily, as described generally in the above-referenced U.S. Pat. No. 4,981,784, may also be constructed using the sequences of the present invention. Such chimeras comprise an N-terminal domain, a ligand-binding domain, and a DNA-binding domain independently selected from two or more receptors of the superfamily. The chimeric receptors are useful, for example, in trans-activation assays, as are well known in the art.

As employed herein, the term "retinoids" refers to naturally occurring compounds with vitamin A activity synthetic analogs and various metabolites thereof. The retinoids are a class of compounds consisting of four isoprenoid units joined in head-to-tail manner. Numerous retinoids have been identified, as described, for example, by Sporn, Roberts and Goodman in the two volume treatise entitled *The Retinoids* (Academic Press, NY, 1984), to which the reader is directed for further detail. Exemplary retinoids include retinol, retinyl acetate, retinyl hexadecanoate, α-retinyl, 4,14-retroretinol, deoxyretinol, anhydroretinol, 3,4-didehydroretinol, 15,15-dimethyl retinol, retinyl methyl ether, retinyl phosphate, mannosyl retinyl phosphate, retinol thioacetate, retinal (retinaldehyde), 3,4-didehydroretinal, retinylidene acetylacetone, retinylidene-1,3-cyclopentanedione, retinal oxime, retinaldehyde acetylhydrazone, retinoic acid, 4-hydroxyretinoic acid, 4-oxoretinoic acid, 5,6-dihydroretinoic acid, 5,6-epoxyretinoic acid, 5,8-epoxyretinoic acid, the open-chain $C_{20}$ analog of retinoic acid (i.e., (all-E-3,7,11,15-tetramethyl-2,4,6, 8,10, 2,14-hexadecaheptaenoic acid), 7,8-didehydroretinoic acid, 7,8-dihydroretinoic acid, "$C_{15}$ Acid" (E, E)-3-methyl-5-(2,6,6-trimethyl-2-cyclohexen-1-yl)-2,4-pentanedioic acid), "$C_{17}$ Acid" ((E,E,E)-5-methyl-7-(2,6,6-trimethyl-1-cyclohexen-1-yl)-2,4,6-hepatrienoic acid), "$C_{22}$ Acid" (14'-apo-β, ψ-carotenoic acid), retinoic acid esters (e.g., methyl ester, ethyl ester, etc.), retinoic acid ethylamide, retinoic acid 2-hydroxyethylamide, methyl retinone, "$C_{18}$" Ketone" ((E,E, E)-6-methyl-8-(2,6,6-trimethyl-1-cyclohexen-1-yl)-3,5,7-ocatrien-2-one), and the like.

In addition, according to the present invention, there are provided DNA sequences which encode novel polypeptides as described above.

Further in accordance with the present invention, there are provided DNA constructs which are operative in animal cells in culture to make said polypeptides.

According to a still further embodiment of the present invention, there are provided animal cells in culture which are transformed with DNA constructs (as described above), which are operative in said cells to make receptor polypeptides, by expression of DNA segments which encode the above described polypeptides.

Among the animal cells contemplated for use in the practice of the present invention are those which are further transformed with a reporter vector which comprises:

(a) a promoter that is operable in the cell,
(b) a hormone response element, and
(c) a DNA segment encoding a reporter protein, wherein said reporter protein-encoding DNA segment is operatively linked to said promoter for transcription of said DNA segment, and
wherein said hormone response element is operatively linked to said promoter for activation thereof.

Promoters contemplated for use in the above-described reporter vectors include the delta-MTV, delta-TK, delta-SV, ADH and TK promoter; hormone response elements contemplated for use in the above-described reporter vectors include the palindromic thyroid hormone response element ($TRE_p$) and the beta-retinoic acid response element (β-RARE); and reporter genes contemplated for use in the above-described reporter vectors include chloramphenicol acetyltransferase (CAT), luciferase (LUC) and beta-galactosidase (β-GAL).

Exemplary reporter vectors are well known in the art and include delta-MTV-$TRE_p$-CAT, delta-TK-$TRE_p$-CAT, delta-SV-$TRE_p$-CAT, delta-MTV-$TRE_p$-LUC, delta-TK-$TRE_p$-LUC, delta-SV-$TRE_p$-LUC, ADH-$TRE_p$-CAT, ADH-$TRE_p$-LUC, TK-$TRE_p$-CAT, TK-$TRE_p$-LUC, and the like.

In accordance with the present invention, there is also provided a method of testing a compound for its ability to regulate the transcription-activating properties of the above-described receptor polypeptides, which method comprises assaying for the presence or absence of reporter protein upon contacting of cells containing a reporter vector and receptor polypeptide with said compound; wherein said reporter vector and said receptor polypeptide are as described above.

In accordance with a still further embodiment of the present invention, there are provided various probes, which can be used to identify genes encoding receptors related to those of the present invention. In this regard, particular reference is made to Examples V and VI below. More particularly, the invention provides labeled, single-stranded nucleic acids comprising sequences of at least 20 contiguous bases having substantially the same sequence as any 20 or more contiguous bases selected from:

(i) bases 2–1861, inclusive, of the DNA illustrated in Sequence ID No. 1 [hRXR-α], or
(ii) bases 20–2095, inclusive, of the DNA illustrated in Sequence ID No. 3 [mRXR-α], or
(iii) bases 15–1653, inclusive, of the DNA illustrated in Sequence ID No. 5 [mRXR-γ], or
(iv) the complement of any one of the sequences according to (i), (ii), or (iii).

As employed herein, the term "labeled single-stranded nucleic acid sequences" refers to single-stranded DNA or RNA sequences which have been modified by the addition thereto of a species which renders the "labeled" sequence readily detectable from among other unmodified sequences. Exemplary labels include radioactive label (e.g., $^{32}P$, $^{35}S$), enzymatic label (e.g., biotin), and the like.

Preferred probes contemplated for use in the practice of the present invention are those having at least about 100 contiguous bases selected from the above-described sequences. Especially preferred are probes having in the range of about 198 up to several hundred nucleotides, because greater selectivity is afforded by longer sequences.

The invention also encompasses a method of making the above-described receptor polypeptides, which method comprises culturing suitable host cells which are transformed with an expression vector operable in said cells to express DNA which encodes receptor polypeptide. Suitable hosts contemplated for use in the practice of the present invention include yeast, bacteria, mammalian cells, insect cells, and the like. E. coli is the presently preferred bacterial species. Any of a number of expression vectors are well known to those skilled in the art that could be employed in the method of the invention. Among these are the prokaryotic expression vectors pNH8A, pNH16A and pNH18A available from Stratagene, La Jolla, Calif. USA.

Further information on the invention is provided in the following non-limiting examples and description of an exemplary deposit.

EXAMPLES

Example I

The KpnI/SacI restriction fragment (503 bp) including the DNA-binding domain of hRAR-alpha-encoding DNA [See Giguere et al., Nature 330, 624 (1987); and commonly assigned U.S. patent application Ser. No. 276,536, filed Nov. 30, 1988, now issued as U.S. Pat. No. 4,981,784; and European Patent Application Publication No. 0 325 849, all incorporated herein by reference] was nick-translated and used to screen a lambda-gt11 human liver cDNA library (Kwok et al.,Biochem. 24, 556 (1985)) at low stringency. The hybridization mixture contained 35% formamide, 1X Denhardt's, 5X SSPE (1X SSPE=0.15M NaCl, 10 mM $Na_2HPO_4$ 1 mM EDTA), 0.1% SDS, 10% dextran sulfate, 100 mg/ml denatured salmon sperm DNA and $10^6$ cpm of [$^{32}P$]-labelled probe. Duplicate nitrocellulose filters were hybridized for 16 h at 42° C., washed once at 25° C. for 15 min with 2X SSC (1X SSC=0.15M NaCl, 0.015M sodium citrate), 0.1% SDS and then washed twice at 55° C. for 30 min. in 2X SSC, 0.1% SDS. The filters were autoradiographed for 3 days at −70° C. using an intensifying screen.

Positive clones were isolated, subcloned into pGEM vectors (Promega, Madison, Wis., USA), restriction mapped, and re-subcloned in various sized restriction fragments into M13mp18 and M13mp19 sequencing vectors. DNA sequence was determined by the dideoxy method with Sequenase™ sequencing kit (United States Biochemical, Cleveland, Ohio, USA) and analyzed by University of Wisconsin Genetics Computer Group programs (Devereux et al., Nucl. Acids Res. 12, 387 (1984)). A unique receptor-like sequence was identified and designated lambda-HL3-1.

Lambda-HL3-1 was used as a hybridization probe to rescreen a lambda-gt10 human kidney cDNA library (Arriza et al., Science 237, 268 (1987)) which produced several clones, the longest of which was sequenced and designated lambda-XR3-1. The DNA sequence obtained as an EcoRI-fragment from lambda-XR3-1 has the sequence indicated in Sequence ID No. 1 [hRXRα].

Similar screening of a mouse whole embryo library with the full-length hRXR-alpha clone described above provided additional sequences which encode different isoforms of the RXR-alpha receptor. In addition, the mouse homolog (mouse RXR-alpha) was also identified in this way.

Thus, mRNA was isolated from 14.5 day post-coitus (p.c.) mouse embryos, translated into cDNA, linked with EcoRI/NotI linkers, then inserted into the unique EcoRI site of the cloning vector λ-ZAP (Stratogene). The resulting library was screened at reduced stringency with $^{32}$P-labeled, full length hRXR-alpha as the probe.

The DNA sequences of the resulting clones are set forth as Sequence ID No. 3 [mRXRα] and Sequence ID No. 5 [mRXRγ].

Example II

Amino acid sequences of mRXR-alpha, hRAR-alpha (human retinoic acid receptor-alpha), hER (human estrogen receptor) hTR-beta (human thyroid hormone receptor-beta) and hGR (human glucocorticoid receptor) were aligned using the University of Wisconsin Genetics Computer Group program "Bestfit" (Devereux et al., supra). Regions of significant similarity between mRXR-alpha and the other receptors, i.e., the 66–68 amino acid DNA binding domains and the ligand-binding domains, are presented schematically in FIG. 1 as percent amino acid identity.

Similarly, the amino acid sequences of human RAR-alpha (hRARα), human RAR-beta (hRARβ), human RAR-gamma (hRARγ), human TR-beta (hTRβ) and human RXR-alpha (hRXRα) were aligned. As done in FIG. 1, regions of significant similarity between hRAR-alpha and the other receptors are presented schematically in FIG. 2 as percent amino acid identity.

Figure 3:
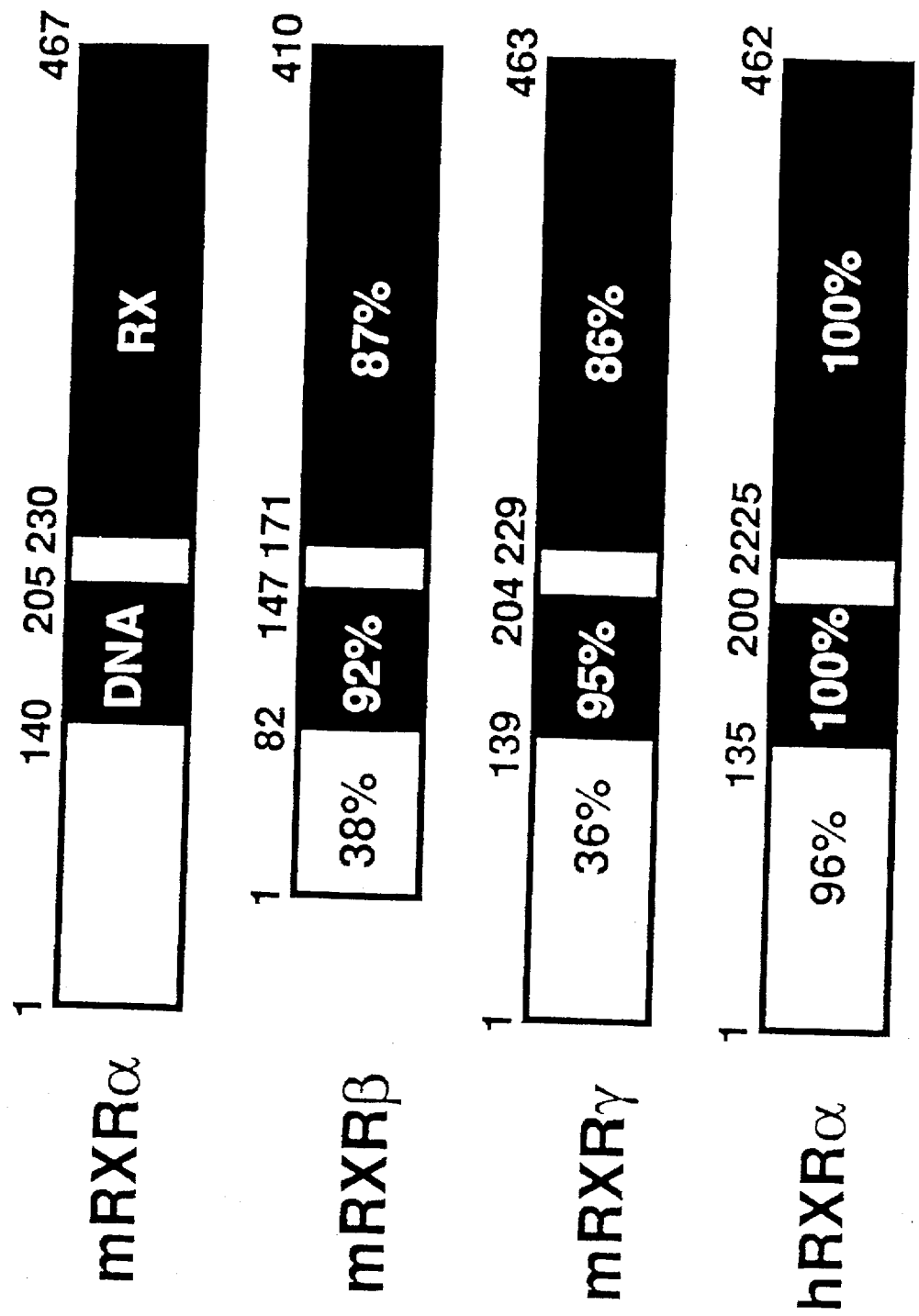
FIG. 3 shows the extent of amino acid identity (i.e., "homology") between the DNA binding domain ("DNA") and ligand binding domain ("RX") of mRXRα, relative to the corresponding domains of mouse RXR-beta (mRXRβ), mouse RXR-gamma (mRXRγ) and hRXRα.

A further comparison of receptors is set forth in FIG. 3. Thus, the amino acid sequences of mouse RXR-alpha (mRXRα), mouse RXR-beta (mRXRβ), mouse RXR-gamma (mRXRγ) and human RXR-alpha (hRXRα) were aligned, and the percent amino acid identity presented schematically in FIG. 3.

Although the DNA-binding domains of both mRXR-alpha and hRXR-alpha are conserved relatively well with respect to other receptors (such as hRAR-alpha and hTR-beta), the ligand binding domain is poorly conserved. (See FIGS. 1 and 3). A comparison between the retinoic acid receptor subfamily of receptors and hRXR-alpha reveals nothing to suggest that hRXR-alpha is related to any of the known retinoid receptors (FIG. 2).

Example III

*Drosophila melanogaster* Schneider line 2 ("S2") cells (Schneider, Embryol. Exp. Morphol. 27, 353 (1972), which are readily available, were seeded at $2 \times 10^6$ per 35 mm$^2$ culture dish and maintained in Schneider medium (GIBCO/Life Technologies, Inc., Grand Island, N.Y., USA) supplemented with penicillin, streptomycin and 12% heat-inactivated fetal bovine serum (Irvine Scientific, Santa Ana, Calif., USA). The cells were transiently co-transfected with 10 μg/dish of plasmid DNA by calcium phosphate precipitation (Krasnow et al., Cell 57, 1031 (1989): 4.5 μg/dish of receptor expression vector or control construct (producing no hRXR-alpha); 0.5 μg/dish of reporter plasmid or control reporter plasmid; 0.5 μg/dish of reference plasmid; and 4.5 μg inert plasmid DNA.

In the receptor expression vector, A5C-RXR-alpha (4.5 μg/dish), receptor hRXR-alpha is constitutively expressed in the S2 cells under the control of the Drosophila actin 5C promoter (A5C; Thummel et al., Gene 74: 445 (1988)) driving transcription of the EcoRI-site-bounded insert of lambda-XR3-1. In the control vector, A5C-RXR$_{rev}$ (also 4.5 μg/ml), the EcoRI-site-bounded insert from lambda-XR3-1 is inserted in the reverse (i.e., non-coding or non-sense-coding) orientation.

A5C-RXR-alpha was made by first inserting at the unique BamHI site of A5C a linker of sequence:

5'-GATCCGATATCCATATGGAATTCGGTACCA, and then inserting, at the EcoRI site of the linker (underlined above), the EcoRI-site-bounded insert of lambda-XR3-1 (See Example I).

The reporter plasmid ADH-TRE$_p$-CAT (at 0.5 μg/dish) contains the palindromic thyroid hormone response element TREp, having the sequence:

5'-AGGTCATGACCT

[(Glass et al. Cell 54, 313 (1988); Thompson and Evans, Proc. Natl. Acad. Sci. (USA) 86, 3494 (1989)], inserted into position -33 (with respect to the transcription start site) of a pD33-ADH-CAT background (Krasnow et al., Cell 57, 1031 (1989)).

pD33-ADH-CAT is a plasmid with the distal promoter of the *Drosophila melanogaster* alcohol dehydrogenase gene linked operably for transcription to the bacterial (*E. coli*) chloramphenicol acetyltransferase ("CAT") gene, a gene for the indicator protein CAT. ADH-TREp-CAT was made by inserting the oligonucleotide of sequence:

5'-CTAGAGGTCATGACCT
TCCAGTACTGGAGATC-5' into the XbaI site at position -33 in pD33-ADH-CAT. pD33-ADH-CAT, without TREp, served as a control reporter (i.e., background) plasmid.

A reference plasmid encoding beta-galactosidase driven by the actin 5C promoter also was transfected (0.5 μg/dish) along with pGEM DNA (4.5 μg/dish) (Promega, Madison, Wis.) to make up the final DNA concentration to 10 μg/dish. The reference plasmid was made by inserting a BamHI-site bounded, beta-galactosidase-encoding segment into the unique BamHI site of A5C. The purpose of the reference plasmid was to normalize results for transfection efficiency.

Twenty-four hours post-transfection, various retinoids were added to the cultures. The retinoids were dissolved in dimethyl-sulfoxide and/or ethanol and the resulting solution was added to 0.1% v/v of culture medium. Initial concentration of the retinoids in the culture media was $10^{-6}$M, except for the experiments underlying the data displayed in FIG. 4, for which varying concentrations of retinoic acid were used.

In control runs, ethanol, at 0.1% v/v in the medium, was used in place of a solution of retinoid.

Cultures were maintained in the dark for 36 hr after addition of retinoid and then harvested. All other parts of the experiments, involving retinoids, were carried out in subdued light.

Cell lysates were centrifuged. Supernatants were assayed for beta-galactosidase, following Herbomel et al., Cell 39, 653–662 (1984), and units/ml of beta-galactosidase activity was calculated. CAT assays (normalized to beta-galactosidase activity) of supernatants were incubated for 75 unit-hours ("units" referring to units of beta-galactosidase activity), as described by Gorman et al., Mol. Cell. Biol. 2, 1044 (1982), usually 150 units for 30 minutes.

No hRXR-alpha dependent activation of CAT expression was noted in any experiment in which control reporter was used in place of ADH-TREp-CAT. Similarly, essentially no activation was observed for runs where control plasmid, A5C-hXR$_{rev}$, was used in place of A5C-hRXR.

The induction of CAT activity in retinoid-treated cells was compared with induction in untreated (i.e., only ethanol-treated) cells. Induction was measured in the presence of retinoic acid (RA), retinal (RAL), retinol acetate (RAC), retinol (ROH), and retinol palmitate (RP). The production of chloramphenicol acetyltransferase (CAT) from the reporter vector (ADH-TREp-CAT) was measured in *Drosophila melanogaster* Schneider line 2 cells, co-transformed with the hRXR-alpha expression vector A5C-RXR-alpha, and exposed to a medium to which retinoic acid (RA), retinal (RAL), retinol acetate (RAC), retinol (ROH), or retinol palmitate (RP) has been added to a concentration of $10^{-6}$M. The relative induction observed was RA>RAL>RAC>ROH>RH.

Figure 4:
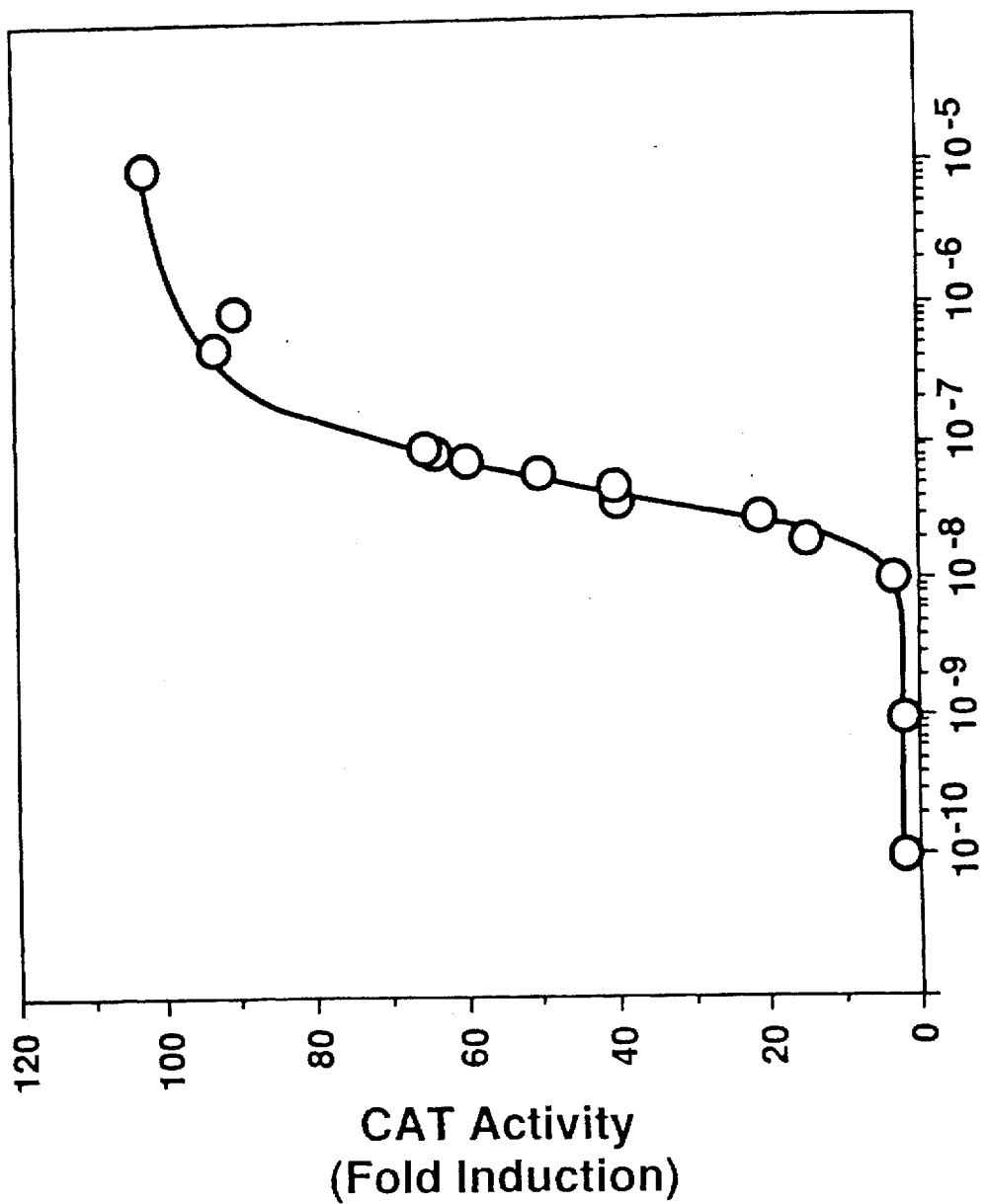
FIG. 4 illustrates the production of CAT from the reporter vector (ADH-TREp-CAT) in *Drosophila melanogaster* Schneider line 2 cells, which are co-transformed with receptor expression vector A5C-RXR-alpha and are in a medium containing various concentrations of retinoic acid.

In FIG. 4 are displayed the results, also expressed in terms of "fold-induction" of CAT activity, as described in the previous paragraph, with retinoic acid at a number of different concentrations, to show the "dose response" of hRXR-alpha (in trans-activation at TREp in insect cells) to retinoic acid in the medium of the cells.

Example IV

This example, describing experiments similar to those described in Example III, shows that hRAR-alpha and hRXR-alpha differ significantly in their properties, specifically with respect to trans-activation of transcription from promoters.

The mammalian receptor-expression vector RS-hRAR-alpha, from which hRAR-alpha is produced under control of the 5'-LTR promoter of the rous sarcoma virus proviral DNA, is described in Giguere et al., Nature 330, 624 (1987); commonly asigned U.S. patent application Ser. No. 276,536, filed Nov. 30, 1988, now issued as U.S. Pat. No. 4,981,784; and European Patent Application Publication No. 0 325 849, all incorporated herein by reference.

The receptor-expression vector RS-hRXR-alpha is constructed similarly to RS-hRAR-alpha, by inserting the EcoRI-site-bounded, hRXR-alpha-encoding segment of lambda-XR3-1 into plasmid pRS (Giguere et al., Cell 46, 645 (1986)).

Control plasmid pRSns is pRS with a non-sense-coding sequence inserted in place of receptor-coding sequence.

Reporter plasmid delta-MTV-TREp-CAT, also known as TREp1MCAT, has also been described (Umesono et al., Nature 336, 262 (1988), Thompson and Evans, supra., see also Umesono and Evans, Cell 57, 1139 (1989). When a control reporter, designated delta-MTV-CAT, which is substantially delta-MTV-TREp-CAT with TREp removed, was used in place of delta-MTV-TREp-CAT, no CAT activity was found with either receptor with any of the retinoids or retinoid analogs.

Reference plasmid, RS-beta-galactosidase, is also known and is substantially the same as RS-hRAR-alpha and RS-hRXR-alpha but has a beta-galactosidase-encoding segment in place of the receptor-encoding segment.

Culture of CV-1 cells, co-transfections (with reporter plasmid, receptor-expression-plasmid or control plasmid, reference plasmid and inert plasmid DNA) and CAT assays were performed as described in Umesono et al., Nature 336, 262 (1988). Co-transfections and CAT assays were carried out by methods similar to those described in Example III. Similar to the experiments in Example III, subdued light was used.

Figure 5:
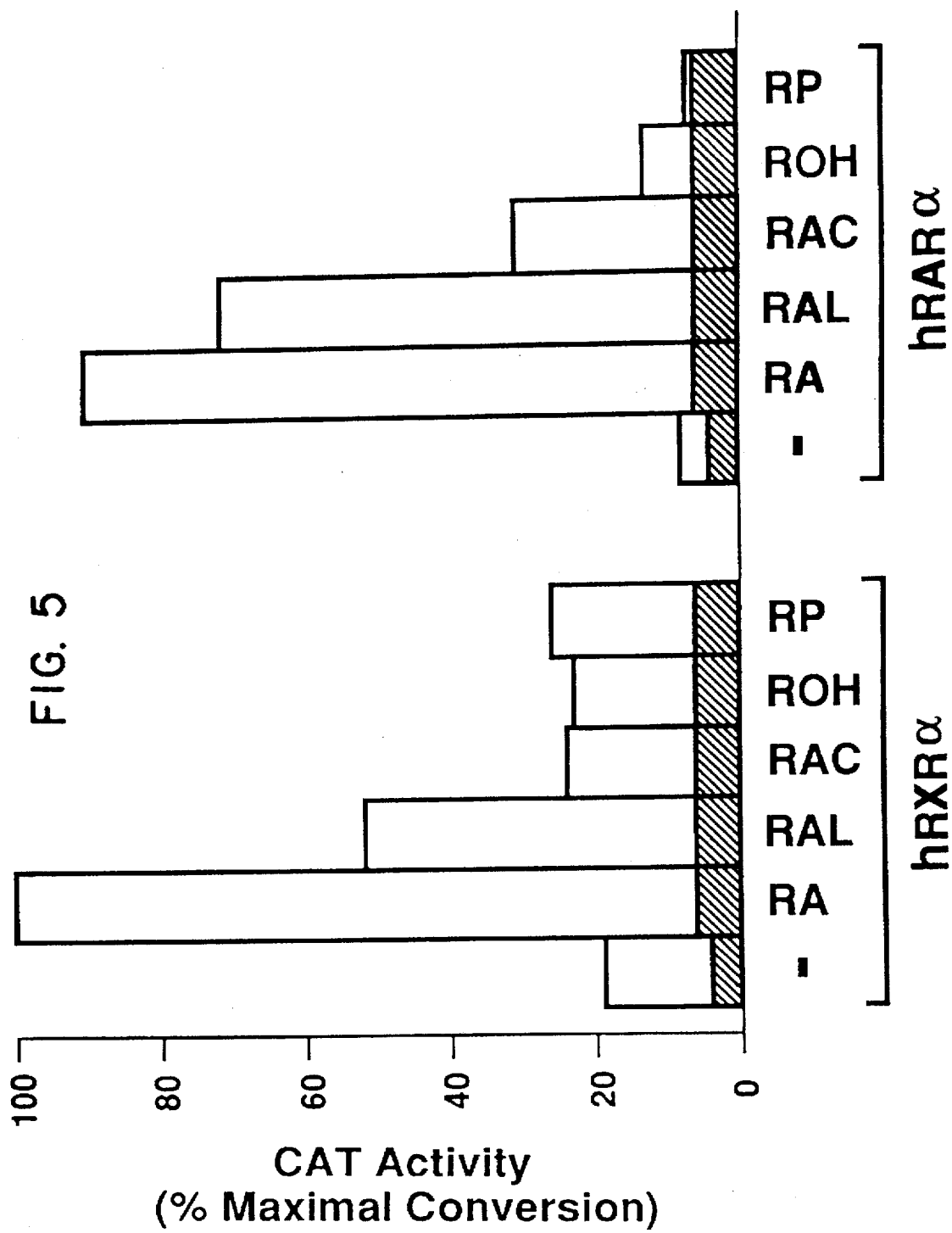
FIG. 5 illustrates the differences in transcription-activating activities of hRXR-alpha and hRAR-alpha, in mammalian cells in culture containing different vitamin A metabolites.

When CV-1 cells co-transformed with reporter plasmid (delta-MTV-TREp-CAT), reference plasmid, control plasmid (i.e., expressing no receptor), and receptor plasmid (RS-hRAR-alpha or RS-hRXR-alpha), were exposed to retinoids RA, RAL, RAC, ROH, RP, (which are naturally occurring vitamin A metabolites), or retinoid-free ethanol, the results shown in FIG. 5 were obtained. The Figure illustrates production of CAT from reporter plasmid in monkey kidney cells of the CV-1 line, which are co-transformed with hRXR-alpha-producing expression vector RS-hRXR-alpha or hRAR-alpha-producing expression vector RS-hRAR. Experiments are carried out in a medium to which RA, RAL, RAC, ROH, or RP has been added to a concentration of $10^{-6}$M. The bars over the "−" sign indicate the levels of CAT production when the cells are exposed to no retinoid (i.e., retinoid-free ethanol). The hatched bars indicate the level of CAT production when a control expression vector, from which no receptor is expressed, is employed in place of the receptor expression vector. The open bars indicate the level of CAT production when receptor-producing expression vector is employed. In each case, the retinoids were added as ethanolic solutions, with the volume of solution 0.1% (v/v) in the medium. Retinoid-free ethanol was added to 0.1% v/v. Results are plotted as percentages of the maximal response observed in the experiments, i.e., hRXR-alpha with RA.

Figure 6:
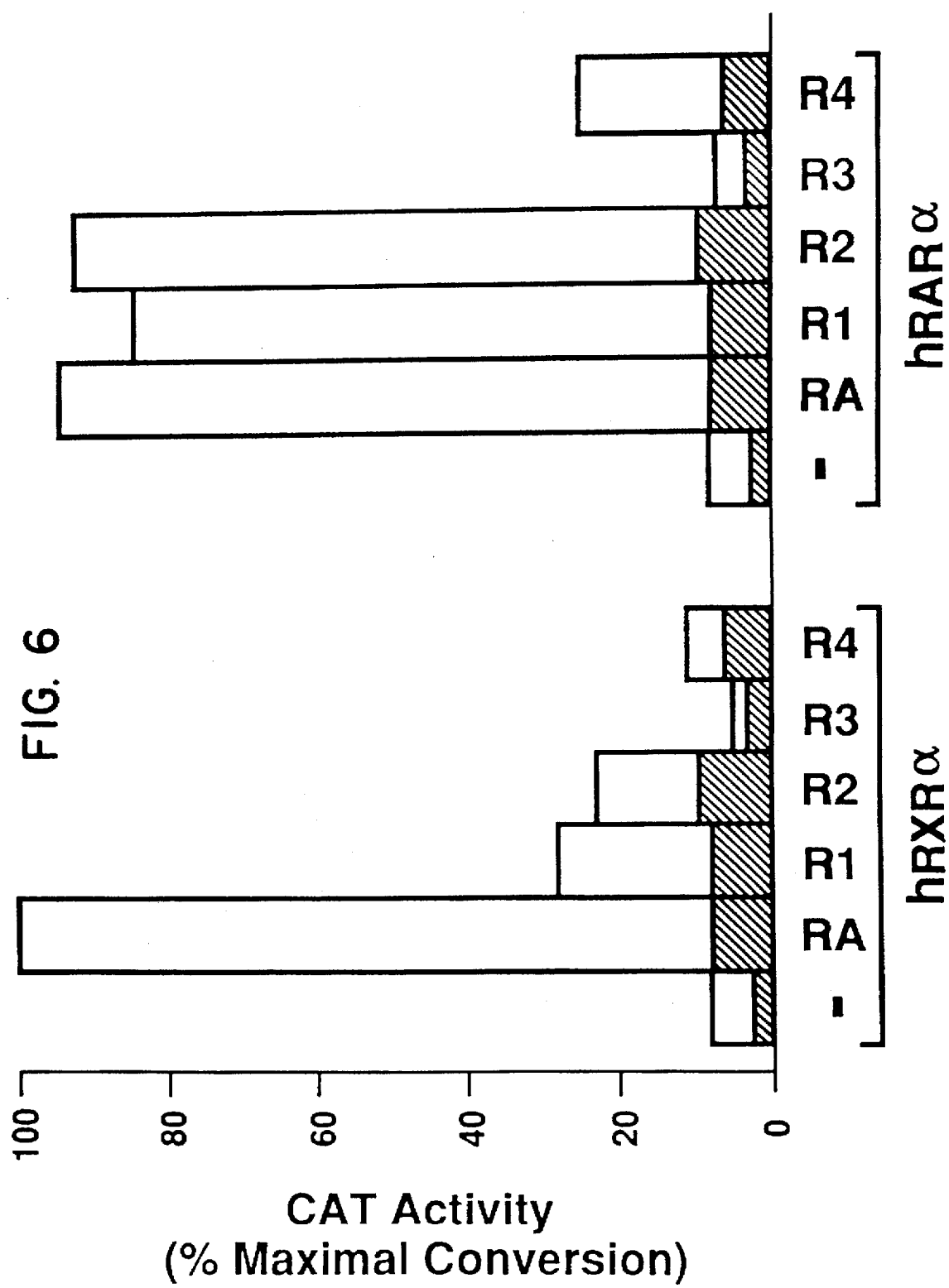
FIG. 6, like FIG. 5, illustrates the differences in transcription-activating activities of hRXR-alpha and hRAR-alpha in mammalian cells in culture containing retinoic acid or different synthetic retinoids.

In FIG. 6, the results are provided for experiments carried out as described in the previous paragraph but with, in place of RAL, RAC, ROH and RP, the synthetic retinoids 4-(5,6,7,8-tetrahydro-5,5,8,8-tetramethyl-4-iodo-2-antrhracenyl)-benzoic acid ("R1"), ethyl-P-[(E)-2-(5,6,7,8-tetrahydro-5,5,8,8-tetramethyl-2-naphthyl) -1-propenyl]-benzoic acid ("R2"), ethyl-all trans-9-(4-methoxy-2,3,6-trimethyl)-3,7-dimethyl-2,4,6,8-nonatetranoate ("R3"), and ethyl-all trans-9-(4-methoxy-2,3,6-trimethyl)-3,7-dimethyl-2,4,6,8-nonatetraenoic acid ("R4") initially at a concentration of $10^{-6}$M. The Figure illustrates production of CAT from the reporter plasmid (delta-MTV-TREp-CAT), CV-1 cells, which are co-transformed with hRXR-alpha-producing expression vector RS-hRXR-alpha or the constitutive hRAR-alpha-producing expression vector RS-hRAR. Experiments are carried out in a medium to which RA, R1, R2, R3, or R4 has been added to a concentration of $10^{-6}$M. The bars over the "−" sign indicate the levels of CAT production when the cells are exposed to no retinoid. The hatched bars indicate the level of CAT production when a control expression vector, from which no receptor is expressed, is employed in place of the receptor expression vector. The open bars indicate the level of CAT production when receptor-producing expression vector is employed.

Figure 7:
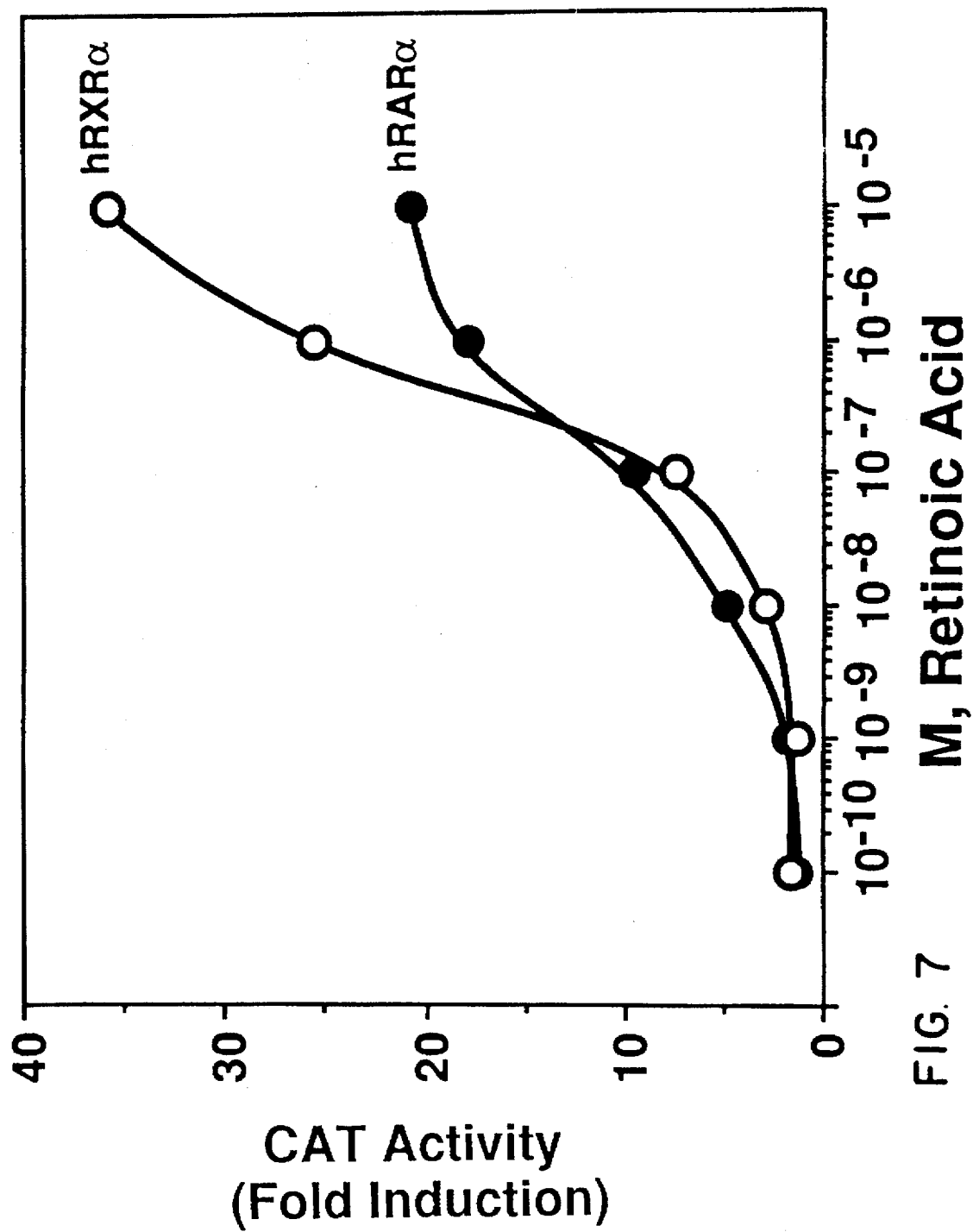
FIG. 7 illustrates the differences between hRXR-alpha and hRAR-alpha in dose-response to retinoic acid in media bathing mammalian cells in which the receptors occur.

In FIG. 7, results are presented for experiments carried out as described in this Example using various concentrations of retinoic acid. The Figure illustrates production of CAT from the reporter plasmid (delta-MTV-TRE$_p$-CAT), in CV-1 cells, which are co-transformed with the receptor-producing expression vector RS-RXR-alpha or RS-RAR-alpha. Experiments are carried out in a medium to which RA has been added to various concentrations. In the Figure, the results are in terms of fold-induction observed with cells exposed to RA, and control cells (exposed to only RA-free ethanol).

Figure 8:
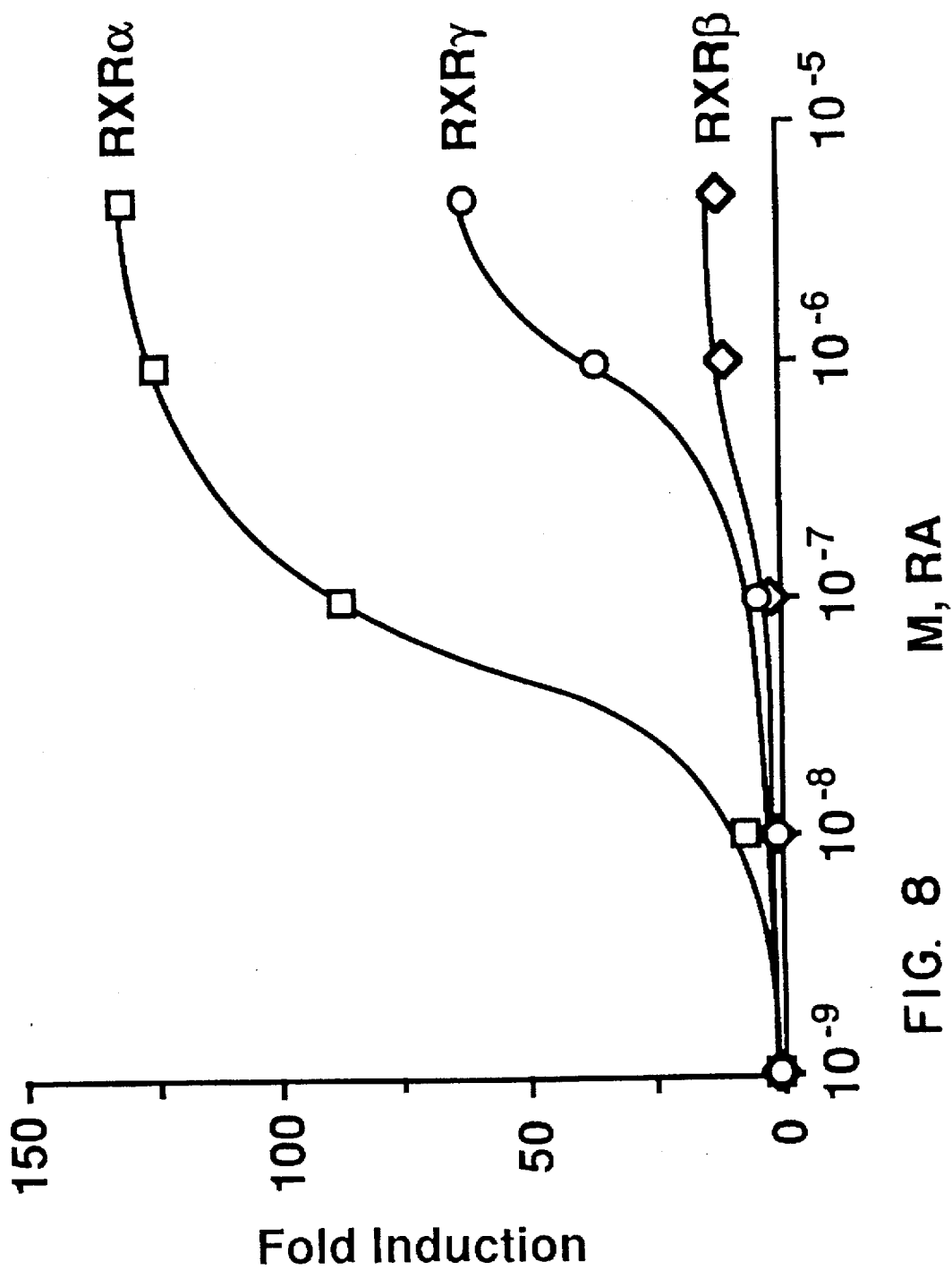
FIG. 8 illustrates the differences between mouse RXR-alpha (mRXRα), mouse RXR-beta (mRXRβ) and mouse RXR-gamma (mRXRγ) in dose response to retinoic acid (RA) in media bathing mammalian cells expressing such receptors.

In FIG. 8, results are presented for experiments carried out as described above, using various concentrations of retinoic acid with expression vectors encoding mRXR-alpha, mRXR-beta and mRXR-gamma.

Figure 9:
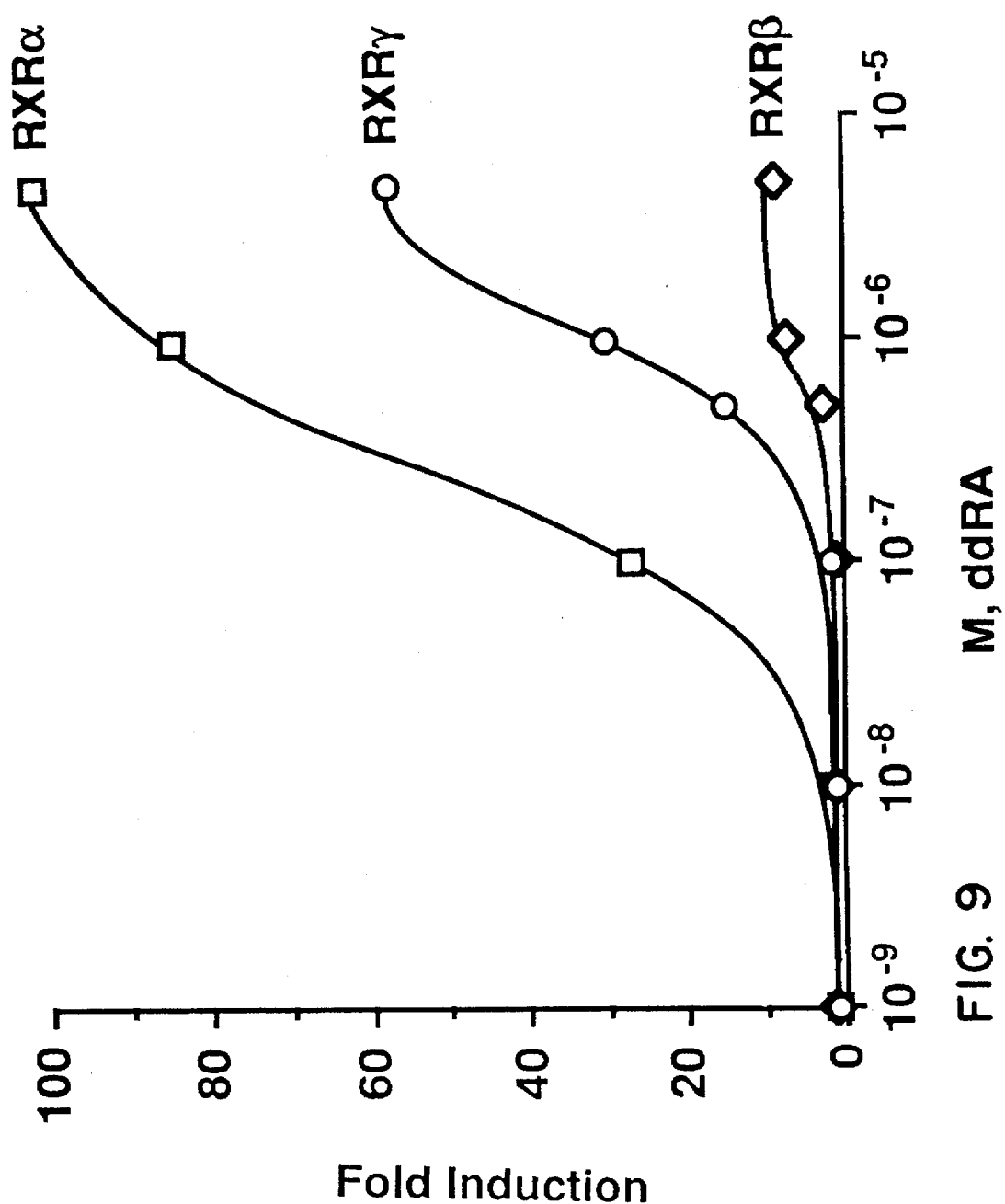
FIG. 9 illustrates the differences between mRXRα, mRXRβ and mRXRγ in dose response to 3,4-didehydroretinoic acid (ddRA) in media bathing mammalian cells expressing such receptors.

In FIG. 9, results are presented for experiments carried out as described above, using various concentrations of 3, 4-didehydroretinoic acid (ddRA) with expression vectors encoding mRXR-alpha, mRXR-beta and mRXR-gamma.

Example V

To determine the distribution of hRXR-alpha gene expression, poly A$^+$ RNAs isolated from a variety of adult rat tissues were size fractionated, transferred to a nylon filter, and hybridized with hRXR-alpha cDNA.

Thus, for each tissue of adult male rat that was analyzed, total RNA was prepared from the tissue (see Chomczynski and Sacchi, Anal. Biochem. 162, 156 (1987)) and poly A$^+$ selected by oligo(dT)-cellulose chromatography. Ten micrograms of poly A$^+$ RNA were separated by 1% agarose-formaldehyde gel electrophoresis, transferred to a Nytran filter (Schleicher and Schuell) (see McDonnell et al., Science 235, 1214 (1987)), and hybridized under stringent conditions with the hRXR-alpha-encoding, EcoRI insert of lambda-XR3-1. Hybridization was performed at 42° C. in a buffer containing 50% formamide, 5X Denhardt's, 5X SSPE, 0.1% SDS, 100mg/ml salmon sperm DNA, 200mg/ml yeast RNA, and [$^{32}$P]-labelled probe. The filter was then washed twice with 2X SSC, 0.1% SDS at 22° C. and twice at 50° C. Autoradiography was for 24 h at −70° C. with an intensifying screen. RNA ladder size markers from Bethesda Research Laboratories (Gaithersburg, Md., USA)

The distribution of RXR-alpha mRNA in the rat reveals a pattern of expression distinct from that of the retinoic acid receptors (Giguere et al., Nature 330, 624 (1987); Zelent et al., Nature 339, 714 (1989); Benbrook, Nature 333,669 (1988)). The rat RXR-alpha message appears to be a single species of about 4.8 kbp (kilobase pairs) which is expressed in many tissues, but most abundantly in the liver, muscle, lung, and kidney and somewhat less abundantly in adrenal, heart, intestine, and spleen.

Example VI

Molecular cloning analyses of the thyroid hormone and retinoic acid receptor genes indicate that each of these receptors belongs to a discrete gene subfamily which encodes several receptor isoforms. To determine if this was also true of RXR, a series of Southern blot analyses were carried out. High stringency hybridization of restriction endonuclease-digested human DNA with a labelled DNA fragment derived from lambda-XR3-1 produced a similar number of bands in every digestion, consistent with a single genetic locus. When the hybridization conditions were relaxed, however, many additional bands were observed in the products of each enzyme digestion. Careful inspection of this hybridization pattern demonstrated that it is unrelated to a similar analysis described for hRAR-alpha (Giguere et al., Nature 330, 624 (1987). These observations indicate the presence of at least one other locus in the human genome related to the hRXR-alpha gene. Further, a genomic DNA zooblot representing mammalian, avian, yeast, and Drosophila species was obtained. Thus far, the RXR gene family appears to be present in all species tested except yeast, which to date has not been shown to contain any members of the steroid receptor superfamily.

For the analyses of human DNA, two human placenta genomic DNA Southern blots were prepared in parallel with identical DNA samples. The blots were hybridized at high or low stringency with a ~1200 bp [$^{32}$P]-labelled fragment of lambda-XR3-1 which included the coding portions of the DNA and ligand binding domains (Sequence ID No. 1, nucleotides 459–1631).

For the zooblot, genomic DNA from human, monkey, rat, mouse, dog, cow, rabbit, chicken, *S. cerevisiae* and *Drosophila melanogaster* were hybridized at low stringency with a ~330 bp [$^{32}$P]-labelled fragment of lambda-XR3-1 which included the DNA-binding domain (Sequence ID No. 1, nucleotides 459–776). Differently sized bands (in comparison with HindIII-digested lambda DNA for sizing) were found for the various species. The blots for all of the species (including both for D. melanogaster), except yeast, mouse and rabbit appeared to have more than one band.

For the analysis of human DNA, the placental DNA was restricted with BamHI, BglII, EcoRI, HindIII, PstI and PvuII, separated in a 0.8% agarose gel (10 µg per lane) and transferred to nitrocellulose (see McDonnell et al., supra) and hybridized as described below.

For the zooblot, EcoRI-digested DNA from the several species (Clontech, Palo Alto, Calif., USA), other than D. melanogaster, was used for Southern blot analysis. EcoRI- and XhoI-digested D. melanogaster DNA was included also.

Blots were hybridized at 42° C. in the low stringency buffer described in Example I or at high stringency in the same buffer modified by addition of formamide to 50%. Low stringency blots were washed twice at room temperature and twice at 50° C. in 2X SSC, 0.1% SDS. The high stringency blot was washed twice at room temperature in 2X SSC, 0.1% SDS and twice at 65° C. in 0.5X SSC, 0.1% SDS.

Example VII

Northern analysis were carried out on the mouse RXR isoforms alpha, beta and gamma, to determine the tissue distribution of these receptors in adult tissues and in developing embryos.

Thus, mRNA (10 µg) was isolated from various adult rat tissues of from day 10.5-day 18.5 p.c. whole mouse embryos. These samples were subjected to Northern analysis using $^{32}$P-labeled cDNA probes derived from regions specific to mRXRα, mRXRβ, or mRXRγ.

In the adult, the various RXR isoforms are seen to be expressed in both a specific and overlapping distribution pattern.

In the embryo, the various isoforms are highly expressed in what appears to be a specific temporal pattern.

The invention has been described in detail with particular reference to preferred embodiments thereof, but it will be understood that variations and modifications can be effected within the spirit and scope of the invention.

Deposit

Figure 2:
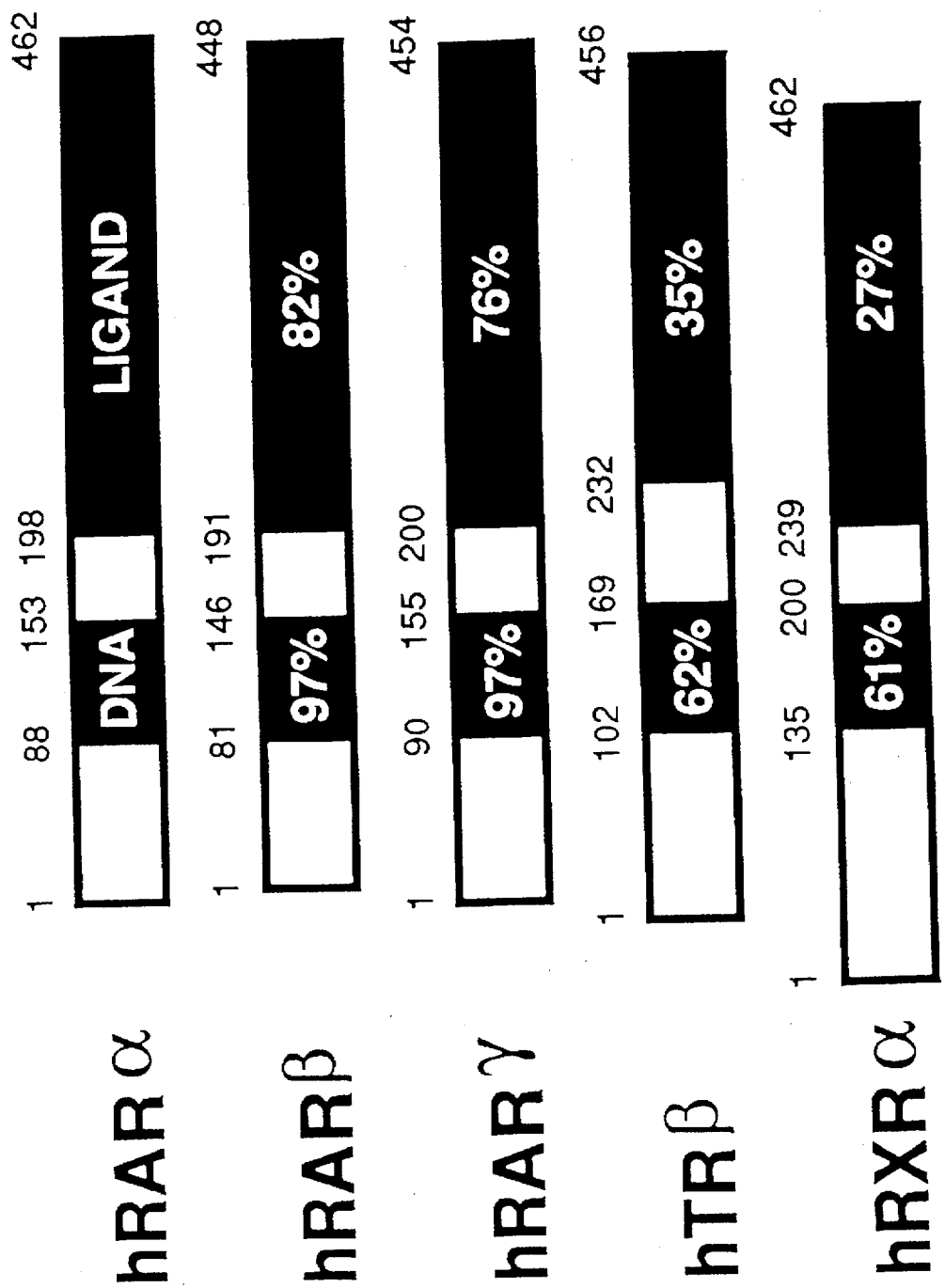
FIG. 2 shows the extent of amino acid identity (i.e., "homology") between the DNA binding domain ("DNA") and ligand binding domain ("LIGAND") of human RAR-alpha (hRARα), relative to the corresponding domains of human retinoic acid receptor-beta (hRARβ), human retinoic acid receptor-gamma (hRARγ), hTRβ and hRXRα.

On Jan. 31, 1990, a sample of replicable phagescript SK double-stranded DNA (Stratagene, La Jolla, Calif., USA), with the 1860 base-pair, EcoRI-site-bounded DNA, the sequence of which is illustrated in FIG. 1, inserted at the unique EcoRI site, was deposited under the terms of the Budapest Treaty on the International Recognition of the Deposit of microorganisms for the Purposes of Patent Procedure at the American Type Culture Collection, Rockville, Md., USA ("ATCC"). The accession number assigned to this deposit is ATCC 40741. The deposited DNA is designated pSK(hRXR-alpha).

Phagescript SK double-stranded DNA is a modified M13mp18 bacteriophage DNA (double-stranded). Derivatives, such as pSK(hRXR-alpha), pSK(mRXR-alpha) and pSK(mRXR-gamma) of phagescript SK double-stranded DNA can be cloned in the same way as M13mp18 and its derivatives.

Samples of pSK(hRXR-alpha) will be publicly available from the ATCC without restriction, except as provided in 37 CFR 1.801 et seq., at the latest on the date an United States Patent first issues on this application or a continuing application thereof. Otherwise, in accordance with the Budapest Treaty and the regulations promulgated thereunder, samples will be available from the ATCC to all persons legally entitled to receive them under the law and regulations of any country or international organization in which an application, claiming priority of this application, is filed or in which a patent based on any such application is granted.

SUMMARY OF SEQUENCES

Sequence ID No. 1 is the coding sequence of an EcoRI-site-bounded DNA segment which encodes the novel receptor disclosed herein, referred to as human RXR-alpha [hRXRα].

Sequence ID No. 2 is the amino acid sequence of the novel receptor referred to herein as hRXRα.

Sequence ID No. 3 is the nucleotide (and amino acid) sequence of the novel receptor disclosed herein, referred to as mouse RXR-alpha [mRXRα].

Sequence ID No. 4 is the amino acid sequence of the novel receptor referred to herein as mRXRα.

Sequence ID No. 5 is the nucleotide (and amino acid) sequence of the novel receptor disclosed herein, referred to as mouse RXR-gamma [mRXRγ].

Sequence ID No. 6 is the amino acid sequence of the novel receptor referred to herein as mRXRγ.

Sequence ID No. 7 is the nucleotide sequence of the receptor disclosed by Hamada, et al in PNAS 86:8298–8293 (1989). This receptor is similar to the receptor referred to herein as mRXRβ.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
    ( A ) LENGTH: 1866 base pairs
    ( B ) TYPE: nucleic acid
    ( C ) STRANDEDNESS: both
    ( D ) TOPOLOGY: both ( i i ) MOLECULE TYPE: cDNA ( i x ) FEATURE:
    ( A ) NAME/KEY: CDS
    ( B ) LOCATION: 76..1464

( x i ) SEQUENCE DESCRIPTION: SEQ ID NO:1:

```
GAATTCCGGC  GCCGGGGGCC  GCCCGCCCGC  CGCCCGCTGC  CTGCGCCGCC  GGCCGGGCAT                    60

GAGTTAGTCG  CAGAC  ATG  GAC  ACC  AAA  CAT  TTC  CTG  CCG  CTC  GAT  TTC  TCC           111
                  Met  Asp  Thr  Lys  His  Phe  Leu  Pro  Leu  Asp  Phe  Ser
                   1                  5                        10

ACC  CAG  GTG  AAC  TCC  TCC  CTC  ACC  TCC  CCG  ACG  GGG  CGA  GGC  TCC  ATG         159
Thr  Gln  Val  Asn  Ser  Ser  Leu  Thr  Ser  Pro  Thr  Gly  Arg  Gly  Ser  Met
               15                      20                      25

GCT  GCC  CCC  TCG  CTG  CAC  CCG  TCC  CTG  GGG  CCT  GGC  ATC  GGC  TCC  CCG         207
Ala  Ala  Pro  Ser  Leu  His  Pro  Ser  Leu  Gly  Pro  Gly  Ile  Gly  Ser  Pro
          30                      35                      40

GGA  CAG  CTG  CAT  TCT  CCC  ATC  AGC  ACC  CTG  AGC  TCC  CCC  ATC  AAC  GGC         255
Gly  Gln  Leu  His  Ser  Pro  Ile  Ser  Thr  Leu  Ser  Ser  Pro  Ile  Asn  Gly
 45                      50                      55                      60

ATG  GGC  CCG  CCT  TTC  TCG  GTC  ATC  AGC  TCC  CCC  ATG  GGC  CCC  CAC  TCC         303
Met  Gly  Pro  Pro  Phe  Ser  Val  Ile  Ser  Ser  Pro  Met  Gly  Pro  His  Ser
                         65                      70                      75

ATG  TCG  GTG  CCC  ACC  ACA  CCC  ACC  CTG  GGC  TTC  AGC  ACT  GGC  AGC  CCC         351
Met  Ser  Val  Pro  Thr  Thr  Pro  Thr  Leu  Gly  Phe  Ser  Thr  Gly  Ser  Pro
               80                      85                      90
```

-continued

| | | | | | | | | | | | | | | | | |
|---|---|---|---|---|---|---|---|---|---|---|---|---|---|---|---|---|
| CAG | CTC | AGC | TCA | CCT | ATG | AAC | CCC | GTC | AGC | AGC | AGC | GAG | GAC | ATC | AAG | 399 |
| Gln | Leu | Ser 95 | Ser | Pro | Met | Asn | Pro 100 | Val | Ser | Ser | Ser | Glu 105 | Asp | Ile | Lys | |
| CCC | CCC | CTG | GGC | CTC | AAT | GGC | GTC | CTC | AAG | GTC | CCC | GCC | CAC | CCC | TCA | 447 |
| Pro | Pro | Leu 110 | Gly | Leu | Asn | Gly | Val 115 | Leu | Lys | Val | Pro 120 | Ala | His | Pro | Ser | |
| GGA | AAC | ATG | GCT | TCC | TTC | ACC | AAG | CAC | ATC | TGC | GCC | ATC | TGC | GGG | GAC | 495 |
| Gly | Asn 125 | Met | Ala | Ser | Phe 130 | Thr | Lys | His | Ile 135 | Cys | Ala | Ile | Cys 140 | Gly | Asp | |
| CGC | TCC | TCA | GGC | AAG | CAC | TAT | GGA | GTG | TAC | AGC | TGC | GAG | GGG | TGC | AAG | 543 |
| Arg | Ser | Ser | Gly | Lys 145 | His | Tyr | Gly | Val | Tyr 150 | Ser | Cys | Glu | Gly | Cys 155 | Lys | |
| GGC | TTC | TTC | AAG | CGG | ACG | GTG | CGC | AAG | GAC | CTG | ACC | TAC | ACC | TGC | CGC | 591 |
| Gly | Phe | Phe | Lys 160 | Arg | Thr | Val | Arg | Lys 165 | Asp | Leu | Thr | Tyr | Thr 170 | Cys | Arg | |
| GAC | AAC | AAG | GAC | TGC | CTG | ATT | GAC | AAG | CGG | CAG | CGG | AAC | CGG | TGC | CAG | 639 |
| Asp | Asn | Lys 175 | Asp | Cys | Leu | Ile | Asp 180 | Lys | Arg | Gln | Arg | Asn 185 | Arg | Cys | Gln | |
| TAC | TGC | CGC | TAC | CAG | AAG | TGC | CTG | GCC | ATG | GGC | ATG | AAG | CGG | GAA | GCC | 687 |
| Tyr | Cys | Arg | Tyr 190 | Gln | Lys | Cys | Leu | Ala 195 | Met | Gly | Met | Lys | Arg 200 | Glu | Ala | |
| GTG | CAG | GAG | GAG | CGG | CAG | CGT | GGC | AAG | GAC | CGG | AAC | GAG | AAT | GAG | GTG | 735 |
| Val 205 | Gln | Glu | Glu | Arg | Gln 210 | Arg | Gly | Lys | Asp | Arg 215 | Asn | Glu | Asn | Glu | Val 220 | |
| GAG | TCG | ACC | AGC | AGC | GCC | AAC | GAG | GAC | ATG | CCG | GTG | GAG | AGG | ATC | CTG | 783 |
| Glu | Ser | Thr | Ser | Ser 225 | Ala | Asn | Glu | Asp | Met 230 | Pro | Val | Glu | Arg | Ile 235 | Leu | |
| GAG | GCT | GAG | CTG | GCC | GTG | GAG | CCC | AAG | ACC | GAG | ACC | TAC | GTG | GAG | GCA | 831 |
| Glu | Ala | Glu | Leu 240 | Ala | Val | Glu | Pro | Lys 245 | Thr | Glu | Thr | Tyr | Val 250 | Glu | Ala | |
| AAC | ATG | GGG | CTG | AAC | CCC | AGC | TCG | CCG | AAC | GAC | CCT | GTC | ACC | AAC | ATT | 879 |
| Asn | Met | Gly 255 | Leu | Asn | Pro | Ser | Ser 260 | Pro | Asn | Asp | Pro | Val 265 | Thr | Asn | Ile | |
| TGC | CAA | GCA | GCC | GAC | AAA | CAG | CTT | TTC | ACC | CTG | GTG | GAG | TGG | GCC | AAG | 927 |
| Cys | Gln | Ala | Ala 270 | Asp | Lys | Gln | Leu | Phe 275 | Thr | Leu | Val | Glu | Trp 280 | Ala | Lys | |
| CGG | ATC | CCA | CAC | TTC | TCA | GAG | CTG | CCC | CTG | GAC | GAC | CAG | GTC | ATC | CTG | 975 |
| Arg 285 | Ile | Pro | His | Phe | Ser 290 | Glu | Leu | Pro | Leu | Asp 295 | Asp | Gln | Val | Ile | Leu 300 | |
| CTG | CGG | GCA | GGC | TGG | AAT | GAG | CTG | CTC | ATC | GCC | TCC | TTC | TCC | CAC | CGC | 1023 |
| Leu | Arg | Ala | Gly | Trp 305 | Asn | Glu | Leu | Leu | Ile 310 | Ala | Ser | Phe | Ser | His 315 | Arg | |
| TCC | ATC | GCC | GTG | AAG | GAC | GGG | ATC | CTC | CTG | GCC | ACC | GGG | CTG | CAC | GTC | 1071 |
| Ser | Ile | Ala | Val 320 | Lys | Asp | Gly | Ile | Leu 325 | Leu | Ala | Thr | Gly | Leu 330 | His | Val | |
| CAC | CGG | AAC | AGC | GCC | CAC | AGC | GCA | GGG | GTG | GGC | GCC | ATC | TTT | GAC | AGG | 1119 |
| His | Arg | Asn 335 | Ser | Ala | His | Ser | Ala 340 | Gly | Val | Gly | Ala | Ile 345 | Phe | Asp | Arg | |
| GTG | CTG | ACG | GAG | CTT | GTG | TCC | AAG | ATG | CGG | GAC | ATG | CAG | ATG | GAC | AAG | 1167 |
| Val | Leu | Thr 350 | Glu | Leu | Val | Ser | Lys 355 | Met | Arg | Asp | Met | Gln 360 | Met | Asp | Lys | |
| ACG | GAG | CTG | GGC | TGC | CTG | CGC | GCC | ATC | GTC | CTC | TTT | AAC | CCT | GAC | TCC | 1215 |
| Thr 365 | Glu | Leu | Gly | Cys | Leu 370 | Arg | Ala | Ile | Val | Leu 375 | Phe | Asn | Pro | Asp | Ser 380 | |
| AAG | GGG | CTC | TCG | AAC | CCG | GCC | GAG | GTG | GAG | GCG | CTG | AGG | GAG | AAG | GTC | 1263 |
| Lys | Gly | Leu | Ser | Asn 385 | Pro | Ala | Glu | Val | Glu 390 | Ala | Leu | Arg | Glu | Lys 395 | Val | |
| TAT | GCG | TCC | TTG | GAG | GCC | TAC | TGC | AAG | CAC | AAG | TAC | CCA | GAG | CAG | CCG | 1311 |
| Tyr | Ala | Ser | Leu 400 | Glu | Ala | Tyr | Cys | Lys 405 | His | Lys | Tyr | Pro | Glu 410 | Gln | Pro | |

| | | | | | | | | | | | | | | | | |
|---|---|---|---|---|---|---|---|---|---|---|---|---|---|---|---|---|
| GGA | AGG | TTC | GCT | AAG | CTC | TTG | CTC | CGC | CTG | CCG | GCT | CTG | CGC | TCC | ATC | 1359 |
| Gly | Arg | Phe | Ala | Lys | Leu | Leu | Leu | Arg | Leu | Pro | Ala | Leu | Arg | Ser | Ile | |
| | | 415 | | | | 420 | | | | | | 425 | | | | |
| GGG | CTC | AAA | TGC | CTG | GAA | CAT | CTC | TTC | TTC | TTC | AAG | CTC | ATC | GGG | GAC | 1407 |
| Gly | Leu | Lys | Cys | Leu | Glu | His | Leu | Phe | Phe | Phe | Lys | Leu | Ile | Gly | Asp | |
| | | 430 | | | | 435 | | | | | 440 | | | | | |
| ACA | CCC | ATT | GAC | ACC | TTC | CTT | ATG | GAG | ATG | CTG | GAG | GCG | CCG | CAC | CAA | 1455 |
| Thr | Pro | Ile | Asp | Thr | Phe | Leu | Met | Glu | Met | Leu | Glu | Ala | Pro | His | Gln | |
| 445 | | | | | | 450 | | | | 455 | | | | | 460 | |
| ATG | ACT | TAGGCCTGCG | GGCCCATCCT | TTGTGCCCAC | CCGTTCTGGC | CACCCTGCCT | | | | | | | | | | 1511 |
| Met | Thr | | | | | | | | | | | | | | | |

| | | | | | |
|---|---|---|---|---|---|
| GGACGCCAGC | TGTTCTTCTC | AGCCTGAGCC | CTGTCCCTGC | CCTTCTCTGC | CTGGCCTGTT | 1571 |
| TGGACTTTGG | GGCACAGCCT | GTCACTGCTC | TGCCTAAGAG | ATGTGTTGTC | ACCCTCCTTA | 1631 |
| TTTCTGTTAC | TACTTGTCTG | TGGCCCAGGG | CAGTGGCTTT | CCTGAGCAGC | AGCCTTCGTG | 1691 |
| GCAAGAACTA | GCGTGAGCCC | AGCCAGGCGC | CTCCCCACCG | GGCTCTCAGG | ACGCCCTGCC | 1751 |
| ACACCCACGG | GGCTTGGGCG | ACTACAGGGT | CTTCGGCCCC | AGCCCTGGAG | CTGCAGGAGT | 1811 |
| TGGGAACGGG | GCTTTTGTTT | CCGTTGCTGT | TTATCGATGC | TGGTTTTCAG | AATTC | 1866 |

(2) INFORMATION FOR SEQ ID NO:2:

(i) SEQUENCE CHARACTERISTICS:
(A) LENGTH: 462 amino acids
(B) TYPE: amino acid
(D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Asp | Thr | Lys | His | Phe | Leu | Pro | Leu | Asp | Phe | Ser | Thr | Gln | Val | Asn |
| 1 | | | | 5 | | | | | 10 | | | | | 15 | |
| Ser | Ser | Leu | Thr | Ser | Pro | Thr | Gly | Arg | Gly | Ser | Met | Ala | Ala | Pro | Ser |
| | | | 20 | | | | | 25 | | | | | 30 | | |
| Leu | His | Pro | Ser | Leu | Gly | Pro | Gly | Ile | Gly | Ser | Pro | Gly | Gln | Leu | His |
| | | | 35 | | | | 40 | | | | | 45 | | | |
| Ser | Pro | Ile | Ser | Thr | Leu | Ser | Ser | Pro | Ile | Asn | Gly | Met | Gly | Pro | Pro |
| | 50 | | | | | 55 | | | | | 60 | | | | |
| Phe | Ser | Val | Ile | Ser | Ser | Pro | Met | Gly | Pro | His | Ser | Met | Ser | Val | Pro |
| 65 | | | | | 70 | | | | | 75 | | | | | 80 |
| Thr | Thr | Pro | Thr | Leu | Gly | Phe | Ser | Thr | Gly | Ser | Pro | Gln | Leu | Ser | Ser |
| | | | | 85 | | | | | 90 | | | | | 95 | |
| Pro | Met | Asn | Pro | Val | Ser | Ser | Ser | Glu | Asp | Ile | Lys | Pro | Pro | Leu | Gly |
| | | | 100 | | | | | 105 | | | | | 110 | | |
| Leu | Asn | Gly | Val | Leu | Lys | Val | Pro | Ala | His | Pro | Ser | Gly | Asn | Met | Ala |
| | | 115 | | | | | 120 | | | | | 125 | | | |
| Ser | Phe | Thr | Lys | His | Ile | Cys | Ala | Ile | Cys | Gly | Asp | Arg | Ser | Ser | Gly |
| | 130 | | | | | 135 | | | | | 140 | | | | |
| Lys | His | Tyr | Gly | Val | Tyr | Ser | Cys | Glu | Gly | Cys | Lys | Gly | Phe | Phe | Lys |
| 145 | | | | | 150 | | | | | 155 | | | | | 160 |
| Arg | Thr | Val | Arg | Lys | Asp | Leu | Thr | Tyr | Thr | Cys | Arg | Asp | Asn | Lys | Asp |
| | | | | 165 | | | | | 170 | | | | | 175 | |
| Cys | Leu | Ile | Asp | Lys | Arg | Gln | Arg | Asn | Arg | Cys | Gln | Tyr | Cys | Arg | Tyr |
| | | | 180 | | | | | 185 | | | | | 190 | | |
| Gln | Lys | Cys | Leu | Ala | Met | Gly | Met | Lys | Arg | Glu | Ala | Val | Gln | Glu | Glu |
| | | 195 | | | | | 200 | | | | | 205 | | | |
| Arg | Gln | Arg | Gly | Lys | Asp | Arg | Asn | Glu | Asn | Glu | Val | Glu | Ser | Thr | Ser |

|  | 210 |  |  |  | 215 |  |  |  |  | 220 |  |  |  |
|---|---|---|---|---|---|---|---|---|---|---|---|---|---|

Ser Ala Asn Glu Asp Met Pro Val Glu Arg Ile Leu Glu Ala Glu Leu
225                     230                     235                     240

Ala Val Glu Pro Lys Thr Glu Thr Tyr Val Glu Ala Asn Met Gly Leu
                245                     250                     255

Asn Pro Ser Ser Pro Asn Asp Pro Val Thr Asn Ile Cys Gln Ala Ala
            260                     265                     270

Asp Lys Gln Leu Phe Thr Leu Val Glu Trp Ala Lys Arg Ile Pro His
        275                     280                     285

Phe Ser Glu Leu Pro Leu Asp Asp Gln Val Ile Leu Leu Arg Ala Gly
    290                     295                     300

Trp Asn Glu Leu Leu Ile Ala Ser Phe Ser His Arg Ser Ile Ala Val
305                     310                     315                     320

Lys Asp Gly Ile Leu Leu Ala Thr Gly Leu His Val His Arg Asn Ser
                325                     330                     335

Ala His Ser Ala Gly Val Gly Ala Ile Phe Asp Arg Val Leu Thr Glu
            340                     345                     350

Leu Val Ser Lys Met Arg Asp Met Gln Met Asp Lys Thr Glu Leu Gly
        355                     360                     365

Cys Leu Arg Ala Ile Val Leu Phe Asn Pro Asp Ser Lys Gly Leu Ser
370                     375                     380

Asn Pro Ala Glu Val Glu Ala Leu Arg Glu Lys Val Tyr Ala Ser Leu
385                     390                     395                     400

Glu Ala Tyr Cys Lys His Lys Tyr Pro Glu Gln Pro Gly Arg Phe Ala
                405                     410                     415

Lys Leu Leu Leu Arg Leu Pro Ala Leu Arg Ser Ile Gly Leu Lys Cys
                420                     425                     430

Leu Glu His Leu Phe Phe Phe Lys Leu Ile Gly Asp Thr Pro Ile Asp
        435                     440                     445

Thr Phe Leu Met Glu Met Leu Glu Ala Pro His Gln Met Thr
    450                     455                     460

( 2 ) INFORMATION FOR SEQ ID NO:3:

( i ) SEQUENCE CHARACTERISTICS:
        ( A ) LENGTH: 2095 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 178..1581

( x i ) SEQUENCE DESCRIPTION: SEQ ID NO:3:

GAATTCGCGG CCGCGGCGAC TTTTGCAACA ACTCGCCGCG CCGCGGCCTC CGCGCGCCGC     60

CGCCGCCGCT GCCGCCGCCG GCTCCCCGCC GCCCGGGCCC CGGGCGGGCC GCGCCGGGGG   120

CCGCCGCGCT GCCGCCCTGC TGCTCCGCCG CCGGCTGGGC ATGAGTTAGT CGCAGAC     177

ATG GAC ACC AAA CAT TTC CTG CCG CTC GAC TTC TCT ACC CAG GTG AAC   225
Met Asp Thr Lys His Phe Leu Pro Leu Asp Phe Ser Thr Gln Val Asn
1               5                   10                  15

TCT TCG TCC CTC AAC TCT CCA ACG GGT CGA GGC TCC ATG GCT GTC CCC   273
Ser Ser Ser Leu Asn Ser Pro Thr Gly Arg Gly Ser Met Ala Val Pro
            20                  25                  30

TCG CTG CAC CCC TCC TTG GGT CCG GGA ATC GGC TCT CCA CTG GGC TCG   321
Ser Leu His Pro Ser Leu Gly Pro Gly Ile Gly Ser Pro Leu Gly Ser

```
CCT GGG CAG CTG CAC TCT CCT ATC AGC ACC CTG AGC TCC CCC ATC AAT    369
Pro Gly Gln Leu His Ser Pro Ile Ser Thr Leu Ser Ser Pro Ile Asn
    50              55              60

GGC ATG GGT CCG CCC TTC TCT GTC ATC AGC TCC CCC ATG GGC CCG CAC    417
Gly Met Gly Pro Pro Phe Ser Val Ile Ser Ser Pro Met Gly Pro His
65              70              75              80

TCC ATG TCG GTA CCC ACC ACA CCC ACA TTG GGC TTC GGG ACT GGT AGC    465
Ser Met Ser Val Pro Thr Thr Pro Thr Leu Gly Phe Gly Thr Gly Ser
                85              90              95

CCC CAG CTC AAT TCA CCC ATG AAC CCT GTG AGC AGC ACT GAG GAT ATC    513
Pro Gln Leu Asn Ser Pro Met Asn Pro Val Ser Ser Thr Glu Asp Ile
            100             105             110

AAG CCG CCA CTA GGC CTC AAT GGC GTC CTC AAG GTT CCT GCC CAT CCC    561
Lys Pro Pro Leu Gly Leu Asn Gly Val Leu Lys Val Pro Ala His Pro
        115             120             125

TCA GGA AAT ATG GCC TCC TTC ACC AAG CAC ATC TGT GCT ATC TGT GGG    609
Ser Gly Asn Met Ala Ser Phe Thr Lys His Ile Cys Ala Ile Cys Gly
    130             135             140

GAC CGC TCC TCA GGC AAA CAC TAT GGG GTA TAC AGT TGT GAG GGC TGC    657
Asp Arg Ser Ser Gly Lys His Tyr Gly Val Tyr Ser Cys Glu Gly Cys
145             150             155             160

AAG GGC TTC TTC AAG AGG ACA GTA CGC AAA GAC CTG ACC TAC ACC TGC    705
Lys Gly Phe Phe Lys Arg Thr Val Arg Lys Asp Leu Thr Tyr Thr Cys
                165             170             175

CGA GAC AAC AAG GAC TGC CTG ATC GAC AAG AGA CAG CGG AAC CGG TGT    753
Arg Asp Asn Lys Asp Cys Leu Ile Asp Lys Arg Gln Arg Asn Arg Cys
            180             185             190

CAG TAC TGC CGC TAC CAG AAG TGC CTG GCC ATG GGC ATG AAG CGG GAA    801
Gln Tyr Cys Arg Tyr Gln Lys Cys Leu Ala Met Gly Met Lys Arg Glu
        195             200             205

GCT GTG CAG GAG GAG CGG CAG CGG GGC AAG GAC CGG AAT GAG AAC GAG    849
Ala Val Gln Glu Glu Arg Gln Arg Gly Lys Asp Arg Asn Glu Asn Glu
    210             215             220

GTG GAG TCC ACC AGC AGT GCC AAC GAG GAC ATG CCT GTA GAG AAG ATT    897
Val Glu Ser Thr Ser Ser Ala Asn Glu Asp Met Pro Val Glu Lys Ile
225             230             235             240

CTG GAA GCC GAG CTT GCT GTC GAG CCC AAG ACT GAG ACA TAC GTG GAG    945
Leu Glu Ala Glu Leu Ala Val Glu Pro Lys Thr Glu Thr Tyr Val Glu
                245             250             255

GCA AAC ATG GGG CTG AAC CCC AGC TCA CCA AAT GAC CCT GTT ACC AAC    993
Ala Asn Met Gly Leu Asn Pro Ser Ser Pro Asn Asp Pro Val Thr Asn
            260             265             270

ATC TGT CAA GCA GCA GAC AAG CAG CTC TTC ACT CTT GTG GAG TGG GCC   1041
Ile Cys Gln Ala Ala Asp Lys Gln Leu Phe Thr Leu Val Glu Trp Ala
        275             280             285

AAG AGG ATC CCA CAC TTT TCT GAG CTG CCC CTA GAC GAC CAG GTC ATC   1089
Lys Arg Ile Pro His Phe Ser Glu Leu Pro Leu Asp Asp Gln Val Ile
    290             295             300

CTG CTA CGG GCA GGC TGG AAC GAG CTG CTG ATC GCC TCC TTC TCC CAC   1137
Leu Leu Arg Ala Gly Trp Asn Glu Leu Leu Ile Ala Ser Phe Ser His
305             310             315             320

CGC TCC ATA GCT GTG AAA GAT GGG ATT CTC CTG GCC ACC GGG CTG CAC   1185
Arg Ser Ile Ala Val Lys Asp Gly Ile Leu Leu Ala Thr Gly Leu His
                325             330             335

GTA CAC CGG AAC AGC GCT CAC AGT GCT GGG GTG GGC GCC ATC TTT GAC   1233
Val His Arg Asn Ser Ala His Ser Ala Gly Val Gly Ala Ile Phe Asp
            340             345             350

AGG GTG CTA ACA GAG CTG GTG TCT AAG ATG CGT GAC ATG CAG ATG GAC   1281
Arg Val Leu Thr Glu Leu Val Ser Lys Met Arg Asp Met Gln Met Asp
```

-continued

|  |  |  | 355 |  |  |  |  | 360 |  |  |  |  | 365 |  |  |  |
|---|---|---|---|---|---|---|---|---|---|---|---|---|---|---|---|---|
| AAG | ACG | GAG | CTG | GGC | TGC | CTG | CGA | GCC | ATT | GTC | CTG | TTC | AAC | CCT | GAC | 1329 |
| Lys | Thr | Glu | Leu | Gly | Cys | Leu | Arg | Ala | Ile | Val | Leu | Phe | Asn | Pro | Asp |  |
|  | 370 |  |  |  | 375 |  |  |  |  | 380 |  |  |  |  |  |  |
| TCT | AAG | GGG | CTC | TCA | AAC | CCT | GCT | GAG | GTG | GAG | GCG | TTG | AGG | GAG | AAG | 1377 |
| Ser | Lys | Gly | Leu | Ser | Asn | Pro | Ala | Glu | Val | Glu | Ala | Leu | Arg | Glu | Lys |  |
| 385 |  |  |  |  | 390 |  |  |  |  | 395 |  |  |  |  | 400 |  |
| GTG | TAT | GCG | TCA | CTA | GAA | GCG | TAC | TGC | AAA | CAC | AAG | TAC | CCT | GAG | CAG | 1425 |
| Val | Tyr | Ala | Ser | Leu | Glu | Ala | Tyr | Cys | Lys | His | Lys | Tyr | Pro | Glu | Gln |  |
|  |  |  |  | 405 |  |  |  |  | 410 |  |  |  |  | 415 |  |  |
| CCG | GGC | AGG | TTT | GCC | AAG | CTG | CTC | CTC | CGC | CTG | CCT | GCA | CTG | CGT | TCC | 1473 |
| Pro | Gly | Arg | Phe | Ala | Lys | Leu | Leu | Leu | Arg | Leu | Pro | Ala | Leu | Arg | Ser |  |
|  |  | 420 |  |  |  |  | 425 |  |  |  |  |  | 430 |  |  |  |
| ATC | GGG | CTC | AAG | TGC | CTG | GAG | CAC | CTG | TTC | TTC | TTC | AAG | CTC | ATC | GGG | 1521 |
| Ile | Gly | Leu | Lys | Cys | Leu | Glu | His | Leu | Phe | Phe | Phe | Lys | Leu | Ile | Gly |  |
|  |  | 435 |  |  |  |  |  | 440 |  |  |  |  |  | 445 |  |  |
| GAC | ACG | CCC | ATC | GAC | ACC | TTC | CTC | ATG | GAG | ATG | CTG | GAG | GCA | CCA | CAT | 1569 |
| Asp | Thr | Pro | Ile | Asp | Thr | Phe | Leu | Met | Glu | Met | Leu | Glu | Ala | Pro | His |  |
|  | 450 |  |  |  |  | 455 |  |  |  |  | 460 |  |  |  |  |  |
| CAA | GCC | ACC | TAGGCCCCCG | CCGCCGTGTG | CCGGTCCCGT | GCCCTGCCTG |  |  |  |  |  |  |  |  |  | 1618 |
| Gln | Ala | Thr |  |  |  |  |  |  |  |  |  |  |  |  |  |  |
| 465 |  |  |  |  |  |  |  |  |  |  |  |  |  |  |  |  |

| GACACAGCTG | CTCAGCTCCA | GCCCTGCCCC | TGCCCTTTCT | GATGGCCCGT | GTGGATCTTT | 1678 |
| GGGGTGCAGT | GTCCTTATGG | GCCCAAAAGA | TGCATCACCA | TCCTCGCCAT | CTTTACTCAT | 1738 |
| GCTTGCCTTT | GGCCCAGGGC | ATAGCAGAGC | TGGTGTGACA | CCTGGCCAGC | TCCTGCCCTA | 1798 |
| CATCAGGCTC | TAAGGCTATG | CTGCTGTCAC | CCCGAGGGTC | GTGGGGTTCG | TCATGGGGCC | 1858 |
| TTCAGCACCT | GGAGCTGCAA | GAGCTGGGAA | AAGGGCTTGT | TCTGGTTGCT | GGTTGCTGGT | 1918 |
| CGCTGGTTCT | CGACATCCCA | CATGGCACCT | CTGTTTGGAG | TGCCCCATCT | TGGCCTGTTC | 1978 |
| AGAGTCCTGG | TACCCAGTTA | GGGTGGGAAT | CCACCTGGGA | TCAAGAAGGA | GCAGGTGGGG | 2038 |
| CAGGCCGTAT | CCTCCTGGGT | CATAGCTAAC | CTATAAAGGC | GCCGCGAATT | CCTCGAG | 2095 |

( 2 ) INFORMATION FOR SEQ ID NO:4:

( i ) SEQUENCE CHARACTERISTICS:
  ( A ) LENGTH: 467 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

| Met | Asp | Thr | Lys | His | Phe | Leu | Pro | Leu | Asp | Phe | Ser | Thr | Gln | Val | Asn |
| 1 |  |  |  | 5 |  |  |  |  | 10 |  |  |  |  | 15 |  |
| Ser | Ser | Ser | Leu | Asn | Ser | Pro | Thr | Gly | Arg | Gly | Ser | Met | Ala | Val | Pro |
|  |  |  | 20 |  |  |  |  | 25 |  |  |  |  | 30 |  |  |
| Ser | Leu | His | Pro | Ser | Leu | Gly | Pro | Gly | Ile | Gly | Ser | Pro | Leu | Gly | Ser |
|  |  | 35 |  |  |  |  | 40 |  |  |  |  | 45 |  |  |  |
| Pro | Gly | Gln | Leu | His | Ser | Pro | Ile | Ser | Thr | Leu | Ser | Ser | Pro | Ile | Asn |
|  | 50 |  |  |  |  | 55 |  |  |  |  | 60 |  |  |  |  |
| Gly | Met | Gly | Pro | Pro | Phe | Ser | Val | Ile | Ser | Ser | Pro | Met | Gly | Pro | His |
| 65 |  |  |  |  | 70 |  |  |  |  | 75 |  |  |  |  | 80 |
| Ser | Met | Ser | Val | Pro | Thr | Thr | Pro | Thr | Leu | Gly | Phe | Gly | Thr | Gly | Ser |
|  |  |  |  | 85 |  |  |  |  | 90 |  |  |  |  | 95 |  |
| Pro | Gln | Leu | Asn | Ser | Pro | Met | Asn | Pro | Val | Ser | Ser | Thr | Glu | Asp | Ile |
|  |  |  | 100 |  |  |  |  | 105 |  |  |  |  | 110 |  |  |
| Lys | Pro | Pro | Leu | Gly | Leu | Asn | Gly | Val | Leu | Lys | Val | Pro | Ala | His | Pro |

```
                    115                         120                         125
Ser  Gly  Asn  Met  Ala  Ser  Phe  Thr  Lys  His  Ile  Cys  Ala  Ile  Cys  Gly
     130                      135                      140

Asp  Arg  Ser  Ser  Gly  Lys  His  Tyr  Gly  Val  Tyr  Ser  Cys  Glu  Gly  Cys
145                           150                      155                     160

Lys  Gly  Phe  Phe  Lys  Arg  Thr  Val  Arg  Lys  Asp  Leu  Thr  Tyr  Thr  Cys
                    165                      170                      175

Arg  Asp  Asn  Lys  Asp  Cys  Leu  Ile  Asp  Lys  Arg  Gln  Arg  Asn  Arg  Cys
               180                      185                      190

Gln  Tyr  Cys  Arg  Tyr  Gln  Lys  Cys  Leu  Ala  Met  Gly  Met  Lys  Arg  Glu
          195                      200                      205

Ala  Val  Gln  Glu  Glu  Arg  Gln  Arg  Gly  Lys  Asp  Arg  Asn  Glu  Asn  Glu
     210                      215                      220

Val  Glu  Ser  Thr  Ser  Ser  Ala  Asn  Glu  Asp  Met  Pro  Val  Glu  Lys  Ile
225                      230                      235                      240

Leu  Glu  Ala  Glu  Leu  Ala  Val  Glu  Pro  Lys  Thr  Glu  Thr  Tyr  Val  Glu
                    245                      250                      255

Ala  Asn  Met  Gly  Leu  Asn  Pro  Ser  Ser  Pro  Asn  Asp  Pro  Val  Thr  Asn
               260                      265                      270

Ile  Cys  Gln  Ala  Ala  Asp  Lys  Gln  Leu  Phe  Thr  Leu  Val  Glu  Trp  Ala
          275                      280                      285

Lys  Arg  Ile  Pro  His  Phe  Ser  Glu  Leu  Pro  Leu  Asp  Asp  Gln  Val  Ile
     290                      295                      300

Leu  Leu  Arg  Ala  Gly  Trp  Asn  Glu  Leu  Leu  Ile  Ala  Ser  Phe  Ser  His
305                      310                      315                      320

Arg  Ser  Ile  Ala  Val  Lys  Asp  Gly  Ile  Leu  Leu  Ala  Thr  Gly  Leu  His
                    325                      330                      335

Val  His  Arg  Asn  Ser  Ala  His  Ser  Ala  Gly  Val  Gly  Ala  Ile  Phe  Asp
               340                      345                      350

Arg  Val  Leu  Thr  Glu  Leu  Val  Ser  Lys  Met  Arg  Asp  Met  Gln  Met  Asp
          355                      360                      365

Lys  Thr  Glu  Leu  Gly  Cys  Leu  Arg  Ala  Ile  Val  Leu  Phe  Asn  Pro  Asp
     370                      375                      380

Ser  Lys  Gly  Leu  Ser  Asn  Pro  Ala  Glu  Val  Glu  Ala  Leu  Arg  Glu  Lys
385                      390                      395                      400

Val  Tyr  Ala  Ser  Leu  Glu  Ala  Tyr  Cys  Lys  His  Lys  Tyr  Pro  Glu  Gln
                    405                      410                      415

Pro  Gly  Arg  Phe  Ala  Lys  Leu  Leu  Leu  Arg  Leu  Pro  Ala  Leu  Arg  Ser
               420                      425                      430

Ile  Gly  Leu  Lys  Cys  Leu  Glu  His  Leu  Phe  Phe  Phe  Lys  Leu  Ile  Gly
          435                      440                      445

Asp  Thr  Pro  Ile  Asp  Thr  Phe  Leu  Met  Glu  Met  Leu  Glu  Ala  Pro  His
     450                      455                      460

Gln  Ala  Thr
465
```

( 2 ) INFORMATION FOR SEQ ID NO:5:

( i ) SEQUENCE CHARACTERISTICS:
    ( A ) LENGTH: 1662 base pairs
    ( B ) TYPE: nucleic acid
    ( C ) STRANDEDNESS: both
    ( D ) TOPOLOGY: both ( i i ) MOLECULE TYPE: cDNA ( i x ) FEATURE:

( A ) NAME/KEY: CDS
( B ) LOCATION: 123..1514

( x i ) SEQUENCE DESCRIPTION: SEQ ID NO:5:

```
GAATTCGCGG CCGCGCTGTG CCTGGGAGCC GAGAGAGAGA GAGAGAGAGA GAGAGAGAGA        60

GAGAGAGAGA GAGAGGCTGT ACTCTTCAGA AGCGCACGAG AGGAATGAAC TGAGCAGCCA       120
```

| | | | | | | | | | | | | | | | |
|---|---|---|---|---|---|---|---|---|---|---|---|---|---|---|---|
| AC | ATG | TAT | GGA | AAT | TAT | TCC | CAC | TTC | ATG | AAG | TTT | CCC | ACC | GGC | TTT | 167
| | Met | Tyr | Gly | Asn | Tyr | Ser | His | Phe | Met | Lys | Phe | Pro | Thr | Gly | Phe |
| | 1 | | | | 5 | | | | | 10 | | | | | 15 |

| GGT | GGC | TCC | CCT | GGT | CAC | ACT | GGC | TCG | ACG | TCC | ATG | AGC | CCT | TCA | GTA | 215
|---|---|---|---|---|---|---|---|---|---|---|---|---|---|---|---|
| Gly | Gly | Ser | Pro | Gly | His | Thr | Gly | Ser | Thr | Ser | Met | Ser | Pro | Ser | Val |
| | | | | 20 | | | | | 25 | | | | | 30 | |

| GCC | TTG | CCC | ACG | GGG | AAG | CCA | ATG | GAC | AGC | CAC | CCC | AGC | TAC | ACA | GAC | 263
|---|---|---|---|---|---|---|---|---|---|---|---|---|---|---|---|
| Ala | Leu | Pro | Thr | Gly | Lys | Pro | Met | Asp | Ser | His | Pro | Ser | Tyr | Thr | Asp |
| | | | 35 | | | | | 40 | | | | | 45 | | |

| ACC | CCA | GTG | AGT | GCC | CCT | CGG | ACG | CTG | AGT | GCT | GTG | GGA | ACC | CCC | CTC | 311
|---|---|---|---|---|---|---|---|---|---|---|---|---|---|---|---|
| Thr | Pro | Val | Ser | Ala | Pro | Arg | Thr | Leu | Ser | Ala | Val | Gly | Thr | Pro | Leu |
| | | 50 | | | | | 55 | | | | | 60 | | | |

| AAT | GCT | CTT | GGC | TCT | CCG | TAT | AGA | GTC | ATC | ACT | TCT | GCC | ATG | GGT | CCA | 359
|---|---|---|---|---|---|---|---|---|---|---|---|---|---|---|---|
| Asn | Ala | Leu | Gly | Ser | Pro | Tyr | Arg | Val | Ile | Thr | Ser | Ala | Met | Gly | Pro |
| | 65 | | | | | 70 | | | | | 75 | | | | |

| CCC | TCA | GGA | GCA | CTG | GCA | GCT | CCT | CCA | GGA | ATC | AAC | TTG | GTG | GCT | CCA | 407
|---|---|---|---|---|---|---|---|---|---|---|---|---|---|---|---|
| Pro | Ser | Gly | Ala | Leu | Ala | Ala | Pro | Pro | Gly | Ile | Asn | Leu | Val | Ala | Pro |
| 80 | | | | | 85 | | | | | 90 | | | | | 95 |

| CCC | AGC | TCC | CAG | CTA | AAT | GTG | GTC | AAC | AGT | GTC | AGC | AGC | TCT | GAG | GAC | 455
|---|---|---|---|---|---|---|---|---|---|---|---|---|---|---|---|
| Pro | Ser | Ser | Gln | Leu | Asn | Val | Val | Asn | Ser | Val | Ser | Ser | Ser | Glu | Asp |
| | | | | 100 | | | | | 105 | | | | | 110 | |

| ATC | AAG | CCC | TTA | CCA | GGT | CTG | CCT | GGG | ATT | GGA | AAT | ATG | AAC | TAC | CCA | 503
|---|---|---|---|---|---|---|---|---|---|---|---|---|---|---|---|
| Ile | Lys | Pro | Leu | Pro | Gly | Leu | Pro | Gly | Ile | Gly | Asn | Met | Asn | Tyr | Pro |
| | | | 115 | | | | | 120 | | | | | 125 | | |

| TCC | ACC | AGC | CCT | GGG | TCT | CTG | GTG | AAA | CAC | ATC | TGT | GCC | ATC | TGT | GGG | 551
|---|---|---|---|---|---|---|---|---|---|---|---|---|---|---|---|
| Ser | Thr | Ser | Pro | Gly | Ser | Leu | Val | Lys | His | Ile | Cys | Ala | Ile | Cys | Gly |
| | | 130 | | | | | 135 | | | | | 140 | | | |

| GAC | AGA | TCC | TCA | GGG | AAG | CAC | TAC | GGT | GTG | TAC | AGC | TGT | GAA | GGT | TGC | 599
|---|---|---|---|---|---|---|---|---|---|---|---|---|---|---|---|
| Asp | Arg | Ser | Ser | Gly | Lys | His | Tyr | Gly | Val | Tyr | Ser | Cys | Glu | Gly | Cys |
| | 145 | | | | | 150 | | | | | 155 | | | | |

| AAA | GGC | TTC | TTC | AAA | AGG | ACC | ATC | AGG | AAA | GAT | CTC | ATC | TAC | ACC | TGT | 647
|---|---|---|---|---|---|---|---|---|---|---|---|---|---|---|---|
| Lys | Gly | Phe | Phe | Lys | Arg | Thr | Ile | Arg | Lys | Asp | Leu | Ile | Tyr | Thr | Cys |
| 160 | | | | | 165 | | | | | 170 | | | | | 175 |

| CGG | GAT | AAC | AAA | GAT | TGT | CTC | ATC | GAC | AAG | CGC | CAG | CGC | AAC | CGC | TGC | 695
|---|---|---|---|---|---|---|---|---|---|---|---|---|---|---|---|
| Arg | Asp | Asn | Lys | Asp | Cys | Leu | Ile | Asp | Lys | Arg | Gln | Arg | Asn | Arg | Cys |
| | | | 180 | | | | | 185 | | | | | 190 | | |

| CAG | TAC | TGT | CGC | TAC | CAG | AAG | TGC | CTG | GTC | ATG | GGC | ATG | AAG | CGG | GAA | 743
|---|---|---|---|---|---|---|---|---|---|---|---|---|---|---|---|
| Gln | Tyr | Cys | Arg | Tyr | Gln | Lys | Cys | Leu | Val | Met | Gly | Met | Lys | Arg | Glu |
| | | 195 | | | | | 200 | | | | | 205 | | | |

| GCT | GTG | CAA | GAA | GAA | AGG | CAG | AGG | AGC | CGA | GAG | CGA | GCA | GAG | AGT | GAG | 791
|---|---|---|---|---|---|---|---|---|---|---|---|---|---|---|---|
| Ala | Val | Gln | Glu | Glu | Arg | Gln | Arg | Ser | Arg | Glu | Arg | Ala | Glu | Ser | Glu |
| | 210 | | | | | 215 | | | | | 220 | | | | |

| GCA | GAA | TGT | GCC | AGT | AGT | AGC | CAC | GAA | GAC | ATG | CCC | GTG | GAG | AGG | ATT | 839
|---|---|---|---|---|---|---|---|---|---|---|---|---|---|---|---|
| Ala | Glu | Cys | Ala | Ser | Ser | Ser | His | Glu | Asp | Met | Pro | Val | Glu | Arg | Ile |
| 225 | | | | | 230 | | | | | 235 | | | | | |

| CTA | GAA | GCC | GAA | CTT | GCT | GTG | GAA | CCA | AAG | ACA | GAA | TCC | TAC | GGT | GAC | 887
|---|---|---|---|---|---|---|---|---|---|---|---|---|---|---|---|
| Leu | Glu | Ala | Glu | Leu | Ala | Val | Glu | Pro | Lys | Thr | Glu | Ser | Tyr | Gly | Asp |
| 240 | | | | | 245 | | | | | 250 | | | | | 255 |

| ATG | AAC | GTG | GAG | AAC | TCA | ACA | AAT | GAC | CCT | GTT | ACC | AAC | ATA | TGC | CAT | 935
|---|---|---|---|---|---|---|---|---|---|---|---|---|---|---|---|
| Met | Asn | Val | Glu | Asn | Ser | Thr | Asn | Asp | Pro | Val | Thr | Asn | Ile | Cys | His |
| | | | 260 | | | | | 265 | | | | | 270 | | |

| GCT | GCA | GAT | AAG | CAA | CTT | TTC | ACC | CTC | GTT | GAG | TGG | GCC | AAA | CGC | ATC | 983
|---|---|---|---|---|---|---|---|---|---|---|---|---|---|---|---|
| Ala | Ala | Asp | Lys | Gln | Leu | Phe | Thr | Leu | Val | Glu | Trp | Ala | Lys | Arg | Ile |
| | | 275 | | | | | 280 | | | | | 285 | | | |

| | | | | | | | | | | | | | | | |
|---|---|---|---|---|---|---|---|---|---|---|---|---|---|---|---|
| CCC | CAC | TTC | TCA | GAT | CTC | ACC | TTG | GAG | GAC | CAG | GTC | ATT | CTA | CTC | CGG | 1031
| Pro | His | Phe | Ser | Asp | Leu | Thr | Leu | Glu | Asp | Gln | Val | Ile | Leu | Leu | Arg |
| | | 290 | | | | 295 | | | | | 300 | | | | |
| GCA | GGG | TGG | AAT | GAA | CTG | CTC | ATT | GCC | TCC | TTC | TCC | CAC | CGC | TCG | GTT | 1079
| Ala | Gly | Trp | Asn | Glu | Leu | Leu | Ile | Ala | Ser | Phe | Ser | His | Arg | Ser | Val |
| | 305 | | | | | 310 | | | | | 315 | | | | |
| TCC | GTC | CAG | GAT | GGC | ATC | CTG | CTG | GCC | ACG | GGC | CTC | CAC | GTG | CAC | AGG | 1127
| Ser | Val | Gln | Asp | Gly | Ile | Leu | Leu | Ala | Thr | Gly | Leu | His | Val | His | Arg |
| 320 | | | | | 325 | | | | | 330 | | | | | 335 |
| AGC | AGC | GCT | CAC | AGC | CGG | GGA | GTC | GGC | TCC | ATC | TTC | GAC | AGA | GTC | CTT | 1175
| Ser | Ser | Ala | His | Ser | Arg | Gly | Val | Gly | Ser | Ile | Phe | Asp | Arg | Val | Leu |
| | | | | 340 | | | | | 345 | | | | | 350 | |
| ACA | GAG | TTG | GTG | TCC | AAG | ATG | AAA | GAC | ATG | CAG | ATG | GAT | AAG | TCA | GAG | 1223
| Thr | Glu | Leu | Val | Ser | Lys | Met | Lys | Asp | Met | Gln | Met | Asp | Lys | Ser | Glu |
| | | | | 355 | | | | 360 | | | | | 365 | | |
| CTG | GGG | TGC | CTA | CGG | GCC | ATC | GTG | CTG | TTT | AAC | CCA | GAT | GCC | AAG | GGT | 1271
| Leu | Gly | Cys | Leu | Arg | Ala | Ile | Val | Leu | Phe | Asn | Pro | Asp | Ala | Lys | Gly |
| | | 370 | | | | | 375 | | | | | 380 | | | |
| TTA | TCC | AAC | CCC | TCT | GAG | GTG | GAG | ACT | CTT | CGA | GAG | AAG | GTT | TAT | GCC | 1319
| Leu | Ser | Asn | Pro | Ser | Glu | Val | Glu | Thr | Leu | Arg | Glu | Lys | Val | Tyr | Ala |
| | 385 | | | | | 390 | | | | | 395 | | | | |
| ACC | CTG | GAG | GCC | TAT | ACC | AAG | CAG | AAG | TAT | CCG | GAA | CAG | CCA | GGC | AGG | 1367
| Thr | Leu | Glu | Ala | Tyr | Thr | Lys | Gln | Lys | Tyr | Pro | Glu | Gln | Pro | Gly | Arg |
| 400 | | | | | 405 | | | | | 410 | | | | | 415 |
| TTT | GCC | AAG | CTT | CTG | CTG | CGT | CTC | CCT | GCT | CTG | CGC | TCC | ATC | GGC | TTG | 1415
| Phe | Ala | Lys | Leu | Leu | Leu | Arg | Leu | Pro | Ala | Leu | Arg | Ser | Ile | Gly | Leu |
| | | | | 420 | | | | | 425 | | | | | 430 | |
| AAA | TGC | CTG | GAA | CAC | CTC | TTC | TTC | TTC | AAG | CTC | ATT | GGA | GAC | ACT | CCC | 1463
| Lys | Cys | Leu | Glu | His | Leu | Phe | Phe | Phe | Lys | Leu | Ile | Gly | Asp | Thr | Pro |
| | | | 435 | | | | | 440 | | | | | 445 | | |
| ATC | GAC | AGC | TTC | CTC | ATG | GAG | ATG | TTG | GAG | ACC | CCA | CTG | CAG | ATC | ACC | 1511
| Ile | Asp | Ser | Phe | Leu | Met | Glu | Met | Leu | Glu | Thr | Pro | Leu | Gln | Ile | Thr |
| | | 450 | | | | 455 | | | | | 460 | | | | |

| | | | | |
|---|---|---|---|---|
| TGAACCTCCT | CAGCTGCAGC | TTCCCCACCC | AGGGTGACCC | TTGGGCGGGT GTGTGTGTGT | 1571
| GGCCCTACCC | TGCACACTCT | CCCCCATCTT | CCACTCTGGC | CTCCCTTCCT GTCCCCAAAA | 1631
| TGTGATGCTT | GTAATAAGCG | GCCGCGAATT | C | | 1662

( 2 ) INFORMATION FOR SEQ ID NO:6:

( i ) SEQUENCE CHARACTERISTICS:
      ( A ) LENGTH: 463 amino acids
      ( B ) TYPE: amino acid
      ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Tyr | Gly | Asn | Tyr | Ser | His | Phe | Met | Lys | Phe | Pro | Thr | Gly | Phe | Gly |
| 1 | | | | 5 | | | | | 10 | | | | | 15 | |
| Gly | Ser | Pro | Gly | His | Thr | Gly | Ser | Thr | Ser | Met | Ser | Pro | Ser | Val | Ala |
| | | | 20 | | | | | 25 | | | | | 30 | | |
| Leu | Pro | Thr | Gly | Lys | Pro | Met | Asp | Ser | His | Pro | Ser | Tyr | Thr | Asp | Thr |
| | | | 35 | | | | 40 | | | | | 45 | | | |
| Pro | Val | Ser | Ala | Pro | Arg | Thr | Leu | Ser | Ala | Val | Gly | Thr | Pro | Leu | Asn |
| | | 50 | | | | | 55 | | | | | 60 | | | |
| Ala | Leu | Gly | Ser | Pro | Tyr | Arg | Val | Ile | Thr | Ser | Ala | Met | Gly | Pro | Pro |
| 65 | | | | | 70 | | | | | 75 | | | | | 80 |
| Ser | Gly | Ala | Leu | Ala | Ala | Pro | Pro | Gly | Ile | Asn | Leu | Val | Ala | Pro | Pro |
| | | | | 85 | | | | | 90 | | | | | 95 | |

```
Ser  Ser  Gln  Leu  Asn  Val  Val  Asn  Ser  Val  Ser  Ser  Ser  Glu  Asp  Ile
               100                      105                      110

Lys  Pro  Leu  Pro  Gly  Leu  Pro  Gly  Ile  Gly  Asn  Met  Asn  Tyr  Pro  Ser
               115                      120                      125

Thr  Ser  Pro  Gly  Ser  Leu  Val  Lys  His  Ile  Cys  Ala  Ile  Cys  Gly  Asp
     130                      135                 140

Arg  Ser  Ser  Gly  Lys  His  Tyr  Gly  Val  Tyr  Ser  Cys  Glu  Gly  Cys  Lys
145                           150                 155                      160

Gly  Phe  Phe  Lys  Arg  Thr  Ile  Arg  Lys  Asp  Leu  Ile  Tyr  Thr  Cys  Arg
                    165                      170                      175

Asp  Asn  Lys  Asp  Cys  Leu  Ile  Asp  Lys  Arg  Gln  Arg  Asn  Arg  Cys  Gln
               180                      185                      190

Tyr  Cys  Arg  Tyr  Gln  Lys  Cys  Leu  Val  Met  Gly  Met  Lys  Arg  Glu  Ala
          195                      200                      205

Val  Gln  Glu  Glu  Arg  Gln  Arg  Ser  Arg  Glu  Arg  Ala  Glu  Ser  Glu  Ala
     210                      215                      220

Glu  Cys  Ala  Ser  Ser  His  Glu  Asp  Met  Pro  Val  Glu  Arg  Ile  Leu
225                      230                      235                      240

Glu  Ala  Glu  Leu  Ala  Val  Glu  Pro  Lys  Thr  Glu  Ser  Tyr  Gly  Asp  Met
               245                      250                      255

Asn  Val  Glu  Asn  Ser  Thr  Asn  Asp  Pro  Val  Thr  Asn  Ile  Cys  His  Ala
               260                      265                      270

Ala  Asp  Lys  Gln  Leu  Phe  Thr  Leu  Val  Glu  Trp  Ala  Lys  Arg  Ile  Pro
               275                      280                      285

His  Phe  Ser  Asp  Leu  Thr  Leu  Glu  Asp  Gln  Val  Ile  Leu  Leu  Arg  Ala
     290                      295                      300

Gly  Trp  Asn  Glu  Leu  Leu  Ile  Ala  Ser  Phe  Ser  His  Arg  Ser  Val  Ser
305                           310                      315                      320

Val  Gln  Asp  Gly  Ile  Leu  Leu  Ala  Thr  Gly  Leu  His  Val  His  Arg  Ser
                    325                      330                      335

Ser  Ala  His  Ser  Arg  Gly  Val  Gly  Ser  Ile  Phe  Asp  Arg  Val  Leu  Thr
               340                      345                      350

Glu  Leu  Val  Ser  Lys  Met  Lys  Asp  Met  Gln  Met  Asp  Lys  Ser  Glu  Leu
          355                      360                      365

Gly  Cys  Leu  Arg  Ala  Ile  Val  Leu  Phe  Asn  Pro  Asp  Ala  Lys  Gly  Leu
370                           375                      380

Ser  Asn  Pro  Ser  Glu  Val  Glu  Thr  Leu  Arg  Glu  Lys  Val  Tyr  Ala  Thr
385                           390                      395                      400

Leu  Glu  Ala  Tyr  Thr  Lys  Gln  Lys  Tyr  Pro  Glu  Gln  Pro  Gly  Arg  Phe
               405                      410                      415

Ala  Lys  Leu  Leu  Leu  Arg  Leu  Pro  Ala  Leu  Arg  Ser  Ile  Gly  Leu  Lys
               420                      425                      430

Cys  Leu  Glu  His  Leu  Phe  Phe  Phe  Lys  Leu  Ile  Gly  Asp  Thr  Pro  Ile
          435                      440                      445

Asp  Ser  Phe  Leu  Met  Glu  Met  Leu  Glu  Thr  Pro  Leu  Gln  Ile  Thr
450                           455                      460
```

( 2 ) INFORMATION FOR SEQ ID NO:7:

( i ) SEQUENCE CHARACTERISTICS:
        ( A ) LENGTH: 2219 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
    ( A ) NAME/KEY: CDS
    ( B ) LOCATION: 109..1341

( x i ) SEQUENCE DESCRIPTION: SEQ ID NO:7:

```
GAATTCCCCC GAAGCCCAGA CAGCTCCTCC CCAAATCCCC TTTCTCAGGG GATCCGTCCG      60

TCTTCTCCTC CTGGCCCACC TCTTACCCCT TCAGCACCTC CACCTCCA ATG CCA CCC     117
                                                    Met Pro Pro
                                                     1

CCG CCA CTG GGC TCC CCC TTC CCA GTC ATC AGT TCT TCC ATG GGG TCC      165
Pro Pro Leu Gly Ser Pro Phe Pro Val Ile Ser Ser Ser Met Gly Ser
         5              10                  15

CCT GGT CTG CCC CCT CCG GCT CCC CCA GGA TTC TCC GGG CCT GTC AGC      213
Pro Gly Leu Pro Pro Pro Ala Pro Pro Gly Phe Ser Gly Pro Val Ser
 20              25                  30                      35

AGC CCT CAG ATC AAC TCC ACA GTG TCG CTC CCT GGG GGT GGG TCT GGC      261
Ser Pro Gln Ile Asn Ser Thr Val Ser Leu Pro Gly Gly Gly Ser Gly
                 40                  45                  50

CCC CCT GAA GAT GTG AAG CCA CCG GTC TTA GGG GTC CGG GGC CTG CAC      309
Pro Pro Glu Asp Val Lys Pro Pro Val Leu Gly Val Arg Gly Leu His
             55                  60                  65

TGT CCA CCC CCT CCA GGT GGT CCT GGG GCT GGC AAA CGG CTC TGT GCA      357
Cys Pro Pro Pro Pro Gly Gly Pro Gly Ala Gly Lys Arg Leu Cys Ala
         70                  75                  80

ATC TGC GGG GAC CGA AGC TCA GGC AAG CAC TAT GGG GTT TAC AGC TGC      405
Ile Cys Gly Asp Arg Ser Ser Gly Lys His Tyr Gly Val Tyr Ser Cys
 85                  90                  95

GAG GGC TGC AAG GGT TTC TTC AAG CGC ACC ATT CGG AAG GAC CTG ACC      453
Glu Gly Cys Lys Gly Phe Phe Lys Arg Thr Ile Arg Lys Asp Leu Thr
100             105                 110                     115

TAC TCG TGT CGT GAT AAC AAA GAC TGT ACA GTG GAC AAG CGC CAG CGG      501
Tyr Ser Cys Arg Asp Asn Lys Asp Cys Thr Val Asp Lys Arg Gln Arg
                120                 125                 130

AAT CGC TGT CAG TAC TGT CGC TAT CAG AAG TGC CTG GCC ACT GGC ATG      549
Asn Arg Cys Gln Tyr Cys Arg Tyr Gln Lys Cys Leu Ala Thr Gly Met
            135                 140                 145

AAA AGG GAG GCG GTT CAG GAG GAG CGT CAA CGG GGG AAG GAC AAA GAC      597
Lys Arg Glu Ala Val Gln Glu Glu Arg Gln Arg Gly Lys Asp Lys Asp
        150                 155                 160

GGG GAT GGA GAT GGG GCT GGG GGA GCC CCT GAG GAG ATG CCT GTG GAC      645
Gly Asp Gly Asp Gly Ala Gly Gly Ala Pro Glu Glu Met Pro Val Asp
165                 170                 175

AGG ATC CTG GAG GCA GAG CTT GCT GTG GAG CAG AAG AGT GAC CAA GGC      693
Arg Ile Leu Glu Ala Glu Leu Ala Val Glu Gln Lys Ser Asp Gln Gly
180             185                 190                     195

GTT GAG GGT CCT GGG GCC ACC GGG GGT GGT GGC AGC AGC CCA AAT GAC      741
Val Glu Gly Pro Gly Ala Thr Gly Gly Gly Gly Ser Ser Pro Asn Asp
                200                 205                 210

CCA GTG ACT AAC ATC TGC CAG GCA GCT GAC AAA CAG CTG TTC ACA CTC      789
Pro Val Thr Asn Ile Cys Gln Ala Ala Asp Lys Gln Leu Phe Thr Leu
            215                 220                 225

GTT GAG TGG GCA AAG AGG ATC CCG CAC TTC TCC TCC CTA CCT CTG GAC      837
Val Glu Trp Ala Lys Arg Ile Pro His Phe Ser Ser Leu Pro Leu Asp
        230                 235                 240

GAT CAG GTC ATA CTG CTG CGG GCA GGC TGG AAC GAG CTC CTC ATT GCG      885
Asp Gln Val Ile Leu Leu Arg Ala Gly Trp Asn Glu Leu Leu Ile Ala
    245                 250                 255

TCC TTC TCC CAT CGG TCC ATT GAT GTC CGA GAT GGC ATC CTC CTG GCC      933
Ser Phe Ser His Arg Ser Ile Asp Val Arg Asp Gly Ile Leu Leu Ala
260                 265                 270                 275
```

-continued

| | | | | | | | | | | | | | | | | |
|---|---|---|---|---|---|---|---|---|---|---|---|---|---|---|---|---|
| ACG | GGT | CTT | CAT | GTG | CAC | AGA | AAC | TCA | GCC | CAT | TCC | GCA | GGC | GTG | GGA | 981 |
| Thr | Gly | Leu | His | Val 280 | His | Arg | Asn | Ser | Ala 285 | His | Ser | Ala | Gly | Val 290 | Gly | |
| GCC | ATC | TTT | GAT | CGG | GTG | CTG | ACA | GAG | CTA | GTG | TCC | AAA | ATG | CGT | GAC | 1029 |
| Ala | Ile | Phe | Asp 295 | Arg | Val | Leu | Thr | Glu 300 | Leu | Val | Ser | Lys | Met 305 | Arg | Asp | |
| ATG | AGG | ATG | GAC | AAG | ACA | GAG | CTT | GGC | TGC | CTG | CGG | GCA | ATC | ATA | CTG | 1077 |
| Met | Arg | Met 310 | Asp | Lys | Thr | Glu | Leu | Gly 315 | Cys | Leu | Arg | Ala | Ile 320 | Ile | Leu | |
| TTT | AAT | CCA | GAC | GCC | AAG | GGC | CTC | TCC | AAC | CCT | GGA | GAG | GTG | GAG | ATC | 1125 |
| Phe | Asn 325 | Pro | Asp | Ala | Lys | Gly 330 | Leu | Ser | Asn | Pro | Gly 335 | Glu | Val | Glu | Ile | |
| CTT | CGG | GAG | AAG | GTG | TAC | GCC | TCA | CTG | GAG | ACC | TAT | TGC | AAG | CAG | AAG | 1173 |
| Leu 340 | Arg | Glu | Lys | Val | Tyr 345 | Ala | Ser | Leu | Glu | Thr 350 | Tyr | Cys | Lys | Gln | Lys 355 | |
| TAC | CCT | GAG | CAG | CAG | GGC | CGG | TTT | GCC | AAG | CTG | CTG | TTA | CGT | CTT | CCT | 1221 |
| Tyr | Pro | Glu | Gln | Gln 360 | Gly | Arg | Phe | Ala | Lys 365 | Leu | Leu | Leu | Arg | Leu 370 | Pro | |
| GCC | CTC | CGC | TCC | ATC | GGC | CTC | AAG | TGT | CTG | GAG | CAC | CTG | TTC | TTC | TTC | 1269 |
| Ala | Leu | Arg | Ser 375 | Ile | Gly | Leu | Lys | Cys 380 | Leu | Glu | His | Leu | Phe 385 | Phe | Phe | |
| AAG | CTC | ATT | GGC | GAC | ACC | CCC | ATT | GAC | ACC | TTC | CTC | ATG | GAG | ATG | CTT | 1317 |
| Lys | Leu | Ile 390 | Gly | Asp | Thr | Pro | Ile 395 | Asp | Thr | Phe | Leu | Met 400 | Glu | Met | Leu | |
| GAG | GCT | CCC | CAC | CAG | CTA | GCC | TGAGCCCAGA | TGCACACCGA | GTGTCACTGA | | | | | | | 1368 |
| Glu | Ala | Pro 405 | His | Gln | Leu | Ala 410 | | | | | | | | | | |

| | | | | | |
|---|---|---|---|---|---|
| GGAGGACTTG | AGCCTGGGCA | GGGGGCAGAG | CCATGGGACA | GGTGCAGAGC | AGGAGGGGAC | 1428 |
| TTGCCCAGCC | TGCCAGGGAT | CTGGCAACAC | TTAGCAGGGT | TCGCTTGGTC | TCCAAGTCGA | 1488 |
| AGGGGACCCC | AGATCCCTGT | GAGGACTTTA | TGTCTACCTT | CAGTGGCCTT | GAGTCTCTGA | 1548 |
| ATTTGTCGGG | GTCTCCCATG | GTGCAGGTGA | TTCTTCATCC | TGGCTCCCCA | GCACAAAGCA | 1608 |
| CTGCCCTGCT | TCCTTCTCAT | TTGGCCTCAC | TCCCTTCTGA | AGAGTGGAAC | AGAGCTCCCC | 1668 |
| CAGAAAGGGG | TGTTGTGGGG | CAGGCCCCCC | AAGCTGATGA | TCATGGGAGC | AGGGCTCTGA | 1728 |
| CAGCCTTTAT | CCTCTCAGAC | TTGACAGATG | GGGCAGAGG | AGGGACCTGC | CTCTGTCTCC | 1788 |
| TGTCAGCCCC | ATTTCCACAG | TCCCTCCTGC | AGTCAGACTG | AAGAATAAAG | GGGTAGTGAA | 1848 |
| GGGGCTGCTG | GAGGTGGAGG | AACCCATTGC | TCTTTTAATT | TCCTGTGAGG | AGAGACTGGG | 1908 |
| AGTTAGACTC | AAAGAAGTAC | TGTACATCCC | CAGGTTGACT | TAAATGTCAG | GGCTGGAGAT | 1968 |
| GGCATGTGGG | CAAGGAGGCC | CCTCAGGTGG | GCTGTCCCAA | AGCTCCCTGG | GCTCTGCCTC | 2028 |
| GGGTGGCCCT | ACAGCTCTTC | CCTAGTCTTA | AGCACAGCTA | GGCTGGGAGC | AAGTGGGGAC | 2088 |
| ATTGATGGGG | GTGGCCAGCC | TGCAGAGTTG | GGTGCTGGGC | TGCATGGTTT | TTGCCCTGGA | 2148 |
| CCTCTTTTGG | GGGTTCCCTC | CCATCTTTCA | CTTGCACATA | AAGTTGCTTT | CCAGTTAAAA | 2208 |
| AAAAAAAAA | A | | | | | 2219 |

That which is claimed is:

1. A recombinant, isolated nucleic acid selected from the group consisting of:
   a nucleic acid which encodes a mammalian retinoid X receptor α protein or a mammalian retinoid X receptor γ protein, wherein said nucleic acid is obtained from a mammalian cDNA library, and wherein said nucleic acid hybridizes under stringent conditions with the complementary strand of a DNA having the sequence set forth in SEQ ID NO:1, 3 or 5;
   a nucleic acid which encodes a polypeptide fragment of said α or γ receptor protein, wherein said fragment comprises at least the N-terminal domain, the DNA-binding domain or the ligand-binding domain of said receptor protein; and
   a nucleic acid degenerate with either of the preceding nucleic acids.

2. A nucleic acid encoding a polypeptide comprising a mammalian retinoid X receptor α moiety or a mammalian retinoid X receptor γ moiety, wherein said nucleic acid comprises the sequence of a nucleic acid according to claim 1.

3. A nucleic acid according to claim 2 which encodes a chimeric receptor of the steroid/thyroid hormone receptor superfamily having an N-terminal domain, a DNA-binding domain, and a ligand binding domain, wherein said chimeric receptor comprises at least the N-terminal domain, the DNA-binding domain, or the ligand binding domain of said mammalian retinoid X receptor α protein or said mammalian retinoid X receptor γ protein.

4. Nucleic acid according to claim 1 wherein said protein has an amino acid sequence selected from the group consisting of:

amino acids 1–462 shown in Sequence ID No. 2 (hRXR-α), amino acids 1–467 shown in Sequence ID No. 4 (mRXR-α), and amino acids 1–463 shown in Sequence ID No. 6 (mRXR-γ).

5. Nucleic acid according to claim 1 wherein said protein comprises a portion which comprises an amino acid sequence selected from the group consisting of:

amino acids 135–200 shown in Sequence ID No. 2 (hRXR-α), amino acids 140–205 shown in Sequence ID No. 4 (mRXR-α), and amino acids 139–204 shown in Sequence ID No. 6 (mRXR-γ).

6. Nucleic acid according to claim 1 which comprises a segment having a continuous nucleotide sequence selected from the group consisting of:

nucleotides 76–1464 shown in sequence ID No. 1 (hRXR-α), nucleotides 181–1581 shown in Sequence ID No. 3 (mRXR-α), and nucleotides 123–1514 shown in Sequence ID No. 5 (mRXR-γ).

7. Phagescript SK containing nucleic acid according to claim 6.

8. A recombinant DNA construct comprising:

(i) the nucleic acid encoding mammalian retinoid X receptor α protein or mammalian retinoid X receptor γ protein according to claim 1 operatively linked to (ii) regulatory element(s) operative for transcription of said nucleic acid and expression of said protein in an animal cell in culture.

9. A DNA construct according to claim 8 wherein said regulatory elements are selected from the Drosophila actin 5C promoter (A5C) and the 5'-LTR promoter of the rous sarcoma virus proviral DNA.

10. An animal cell in culture which is transformed with a DNA construct according to claim 8.

11. A cell according to claim 10 wherein said cell is an insect cell or a mammalian cell.

12. A cell according to claim 11 wherein the DNA construct comprises DNA encoding hRXR-alpha, mRXR-alpha or mRXR-gamma under control of the Drosophila actin 5C promoter (A5C) or the 5'-LTR promoter of the rous sarcoma virus proviral DNA.

13. A cell according to claim 10, wherein said cell is further transformed with a reporter vector which comprises:

(a) a promoter that is operable in said cell, (b) a hormone response element, and (c) a DNA segment encoding a reporter protein, wherein said reporter protein-encoding DNA segment is operatively linked to said promoter for transcription of said DNA segment, and wherein said hormone response element is operatively linked to said promoter for activation thereof.

14. A cell according to claim 13 wherein:

the promoter is the 5'-LTR promoter of a mouse mammary tumor virus, the hormone response element is selected from the group consisting of the palindromic thyroid hormone response element ($TRE_p$) and beta-retinoic acid response element (beta-RARE), and the reporter protein is selected from the group consisting of chloramphenicol acetyltransferase, luciferase and beta-galactosidase.

15. A cell according to claim 13 wherein:

the promoter is selected from the group consisting of delta-MTV, delta-TK and delta-SV, the hormone response element is the palindromic thyroid hormone response element ($TRE_p$), and the reporter protein is selected from the group consisting of chloramphenicol acetyltransferase and luciferase.

16. A cell according to claim 13 wherein:

the promoter is selected from the group consisting of promoter ADH and the TK promoter;

the hormone response element is the palindromic thyroid hormone response element ($TRE_p$), and the reporter protein is selected from the group consisting of chloramphenicol acetyltransferase and luciferase.

17. A cell according to claim 16 which is a *Drosophila melanogaster* Schneider line 2 cell.

* * * * *